US005962767A

United States Patent [19]
Ohlrogge et al.

[11] Patent Number: 5,962,767
[45] Date of Patent: *Oct. 5, 1999

[54] STRUCTURE AND EXPRESSION OF AN ARABIDOPSIS ACETYL-COENZYME A CARBOXYLASE GENE

[75] Inventors: John B. Ohlrogge, Okemos; Keith R. Roesler; Basil S. Shorrosh, both of Lansing, all of Mich.

[73] Assignee: Board of Trustees Operating Michigan State University, E. Lansing, Mich.

[*] Notice: This patent is subject to a terminal disclaimer.

[21] Appl. No.: 08/790,519

[22] Filed: Jan. 29, 1997

Related U.S. Application Data

[63] Continuation of application No. 08/248,630, May 24, 1994, abandoned.

[51] Int. Cl.$^6$ .............................. A01H 5/00; A01H 5/10; C12N 15/82; C12N 5/04
[52] U.S. Cl. .................. 800/298; 536/23.6; 435/419; 435/320
[58] Field of Search .................................... 800/205, 250, 800/298, 281, 300; 435/172.3, 419, 320, 468, 430; 536/23.6

[56] References Cited

U.S. PATENT DOCUMENTS

| | | | |
|---|---|---|---|
| 4,874,421 | 10/1989 | Kleschick et al. | 71/9 |
| 5,162,602 | 11/1992 | Somers et al. | 800/235 |
| 5,290,696 | 3/1994 | Somers et al. | 435/240.5 |
| 5,428,001 | 6/1995 | Somers et al. | 504/130 |
| 5,445,952 | 8/1995 | Campbell et al. | 435/121 |
| 5,498,544 | 3/1996 | Gengenbach et al. | 435/320.1 |
| 5,539,092 | 7/1996 | Haselkorn et al. | 536/23.2 |
| 5,559,220 | 9/1996 | Roessler et al. | 536/23.6 |

FOREIGN PATENT DOCUMENTS

| | | |
|---|---|---|
| 0469810 | 2/1992 | European Pat. Off. . |
| 0658622 | 6/1995 | European Pat. Off. . |
| WO 93/11243 | 6/1993 | WIPO . |
| WO 94/17188 | 8/1994 | WIPO . |
| WO 94/23027 | 10/1994 | WIPO . |
| WO 94/29467 | 12/1994 | WIPO . |
| WO 95/29246 | 11/1995 | WIPO . |

OTHER PUBLICATIONS

Al–Feel, W. et al., "Cloning of the Yeast FAS3 Gene and Primary Structure of Yeast Acetyl–CoA Carboxylase," *PNAS (USA)* 89:4534–4538 (1992).

Bettey, M. et al., "Purification and Characterization of Acetyl CoA Carboxylase from Developing Pea Embryos," *J. Plant Physiol.* 140:513–520 (1992).

Cahoon, E.B. et al., "Expression of a Coriander Desaturase Results in Petroselinic Acid Production in Transgenic Tobacco," *PNAS (USA)* 89:11184–11188 (1992).

Cahoon, E.B. et al., "Analysis of Glucocerebrosides of Rye (*Secale cereal* L. cv Puma) Leaf and Plasma Membrane," *Plant Physiol.* 95:58–68 (1991).

Charles, D.J. et al., "Purification and Characterization of Acetyl–CoA Carboxylase from Developing Soybean Seeds," *Phytochem.* 25:1067–1071 (1986).

Charles D.J. et al., "Characterization of Acetyl–CoA Carboxylase in the Seed of Two Soybean Genotypes," *Phytochem.* 25:55–59 (1986).

Deerburg, S. et al., "Synthesis of Medium Chain Fatty Acids and Their Incorporation into Triacylglycerols by Cell Free Fractions from Cuphea Embryos," *Planta.* 180:440–444 (1990).

Devereux, J. et al., "A Comprehensive Set of Sequence Analysis Programs for the VAX," *Nucleic Acids Res.* 12:387–395 (1984).

Ebel, J. et al., "Enzymes of Flavone and Flavonol Glycoside Biosynthesis. Coordinated and Selective Induction in Cell–Suspension Cultures of *Petroselinum Hortense*," *Eur. J. Biochem.* 75:201–209 (1977).

Ebel, J. et al., "Phytoalexin Synthesis in Soybean Cells: Elicitor Induction of Phenylalanine Ammonia–Lyase and Chalcone Synthase mRNAs and Correlation with Phytoalexin Accumulation," *Arch. Biophys.* 232:240–248 (1984).

Egin–Buhler, B. et al., "Improved Purification and Futher Characterization of Acetyl–CoA Carboxylase from Cultured Cells of Parsley (*Petroselinum Hortense*)," *Eur. J. Biochem.* 133:335–339 (1983).

Egli, M.A. et al., "Characterization of Maize Acetyl–Coenzyme A Carboxylase," *Plant Physiol.* 101:499–506 (1993).

Elborough, K.M. et al. "Regulation of Primary Storage Products of Oil Seeds by Manipulating the Level of Genes Involved in Lipid Metabolism or Plant Acetyl CoA Carboxylase," Jan. 4–23, 1994, Supplement 18A (1994) (Abstract #X1–418).

Finlayson, S.A. et al., "Acetyl–Coenzyme A Carboxylase from the Developing Endosperm of *Ricinus Communis*," *Arch. Biochem. Biophys.* 225:576–585 (1983).

Goodall, G.J. et al., "Different Effects of Intron Nucleotide Composition and Secondary Structure of Pre–mRNA Splicing in Monocot and Dicot Plants," *EMBO J.* 10:2635–2644 (1991).

Gornicki, P. et al., "Wheat Acetyl–CoA Carboxylase," *Plant Mol. Biol.* 22:547–552 (1993).

(List continued on next page.)

*Primary Examiner*—Elizabeth F. McElwain
*Attorney, Agent, or Firm*—Lahive & Cockfield LLP

[57] ABSTRACT

An Arabidopsis acetyl-CoA carboxylase (ACCase) gene has been isolated and sequenced. The 10 kb gene encodes a 251 kD cytosolic ACCase isozyme. The nucleic acid sequence of the gene is set forth in SEQ ID No. 1 and has been accorded GenBank Accession No. L27074. The cDNA sequence and deduced amino acid sequence of the cDNA are set forth in SEQ ID Nos. 2 and 3, respectively. By controlling expression of the gene of the present invention, carboxylation of acetyl-CoA to produce malonyl-CoA may be controlled. Thus, by introducing constructs of the gene of the present invention in sense or anti-sense orientation, carboxylation of acetyl-CoA to produce malonyl-CoA may be increased or decreased. Consequently, fatty acid synthesis and elongation in plants and seeds which depends on malonyl-CoA may also be controlled.

14 Claims, 5 Drawing Sheets

OTHER PUBLICATIONS

Hall, T.C. et al., "Messenger RNA for G1 Protein of French Bean Seeds: Cell Free Translation and Product Characterization," *PNAS (USA)* 75:3196–3200 (1978).

Harwood, J.L., "Fatty Acid Metabolism," *Annu. Rev. Plant Physiol. Plant Mol. Biol.* 39:101–138 (1988).

James, D.W., et al., "Isolation of EMS–Induced Mutants in Arabidopsis Altered in Seed Fatty Acid Composition," *Theor. Appl. Genet.* 80:241–245 (1990).

Kannangara, C.G. et al., "Fat Metabolism in Higher Plants. A Procaryotic Type Acetyl CoA Carboxylase in Spinach Chloroplasts," *Arch. Biochem. Biophys.* 152:83–91 (1972).

Keegstra, K. et al., "Chloroplastic Precursors and Their Transport Across the Envelope Membranes," *Annu. Rev. Plant. Physiol. Plant. Mol. Biol.* 40:471–501 (1989).

Kim, K–H. et al., "Role of Reversible Phosphorylation of Acetyl–CoA Carboxylase in Long–Chaing Fatty Acid Synthesis," *FASEB J.* 3:2250–2256 (1989).

Kionka, C. et al., "The Enzymatic Malonation of 1–Amioncyclopropane–1–Carboxylic Acid in Homogenates of Mung–Bean Hypocotyls," *Planta* 162:226–235 (1984).

Laing, W.A. et al., "Activation of Spinach Chloroplast Acetyl–Coenzyme A Carboxylase by Conenzyme A," *FEBS Lett.* 144:341–344 (1982).

Li, S–J. et al., "The Gene Encoding the Biotin Carboxylase Subunit of *Escherichia coli* Acetyl–CoA Carboxylase," *J. Biol. Chem.* 267:855–863 (1992a).

Li, S–J. et al., "The Genes Encoding the Two Carboxyltransferase Subunits of *Escherichia coli* Acetyl–CoA Carboxylase," *J. Biol. Chem.* 267:16841–16847 (1992b).

Liu, Y. et al., "Relationship Betwwen the Malonation of 1–Aminocyclopropane–1–Carboxylic Acid and D–Amino Acids in Mung–Bean Hypocotyls," *Planta* 158:437–441 (1983).

Lopez–Casillas, F. et al., "Structure of the Coding Sequence and Primary Amino Acid Sequence of Acetyl–Coenzyme A Carboxylase," *PNAS (USA)* 85:5784–5788 (1988).

Lutcke, H.A. et al., "Selection of AUG Initiation Codons Differs in Plants and Animals," *EMBO J.* 6:43–48 (1987).

Myers, R.M. et al., "Detection of Single Base Substitutions by Ribonuclease Cleavage at Mismatches in RNA:DNA Duplexes," *Science* 230:1242–1246 (1985).

Pollard, M.R. et al., "Biosynthesis of C20 and C22 Fatty Acids by Developing Seeds of *Limnanthes alba,*" *Plant Physiol.* 66:649–655 (1980).

Post–Beitenmiller, D. et al., "In vivo Pools of Free and Acylated Acyl Carrier Proteins in Spinach. Evidence for SItes of Regulation of Fatty Acid Biosynthesis," *J. Biol. Chem.* 266:1858–1865 (1991).

Post–Beitenmiller, D. et al., "Regulation of Plant Lipid Biosynthesis: An Example of Developmental Regulation Superimposed on a Ubiquitous Pathway," in DPS Ven–na, ed, Control of plant gene expression. CRC press, Boca Raton, Fl, pp. 157–174 (1993).

Post–Beitenmiller, D. et al., "Regulation of Plant Fatty Acid Biosynthesis: Analysis of Acyl–CoA and Acyl–ACP Substrate Pools in Spinach and Pea Chloroplasts," *Plant Physiol.* 100:923–930 (1992).

Post–Beitenmniller, D. et al. "Regulation of Plant Fatty Acid Biosynthesis: Analysis of Acyl–CoA and Acyl–AcP Substrate Pools in Chloroplast Isolated from Pea and Spinach," (Manuscript).

Roessler, P.G. et al., "Cloning and Characterization of the Gene that Encodes Acetyl–Coenzyme A Carboxylase in the Alga *Cyclotella Cryptica.,*" *J. Biol. Chem.* 268:19254–19259 (1993).

Samols, D. et al., "Evolutionary Conservation Among Biotin Enzymes," *J. Biol. Chem.* 263:6461–6464 (1988).

Sasaki, Y. et al., "Chloroplast–Encoded Protein as a Subunit of Acetyl–CoA Carboxylase in Pea Plant," *J. Biol. Chem.* 268:25118–25123 (1993).

Shintani, D.K. et al., "Feedback Regulation of Fatty Acid Synthesis in Tobacco Cell Suspension Cultures," (abstract No. 54) *Plant Physiol.* 102:S–11 (1993).

Shorrosh, B.S. et al., "Molecular Cloning, Characterization, and Elicitation of Acetyl–CoA Carboxylase from Alfalfa," *PNAS (USA)* 91:4323–4327 (1994).

Simcox, P.D. et al., "Respiratory Pathways and Fat Synthesis in the Developing Castor Oil Seed," *Canad. J. Bot.* 57:1008–1014 (1979).

Slabas, A.R. et al., "Rapid Purification of a High Molecular Weight Subunit Polypeptide form of Rape Seed Acetyl CoA Carboxylase," *Plant. Sci.* 39:177–182 (1985).

Somers, D.A. et al., "Expression of Acc1 Gene–Encoded Acetyl–Coenzyme A Carboxylase in Developing Maize (*Zea mays L.*) Kernels," *Plant. Physiol.* 101:1097–1101 (1993).

Takai, T. et al., "Primary Structure of Chicken Liver Acetyl–Coenzyme: A Carboxylase deduced from cDNA Sequence," *J. Biol. Chem.* 263:2651–2657 (1988).

Turnham, E. et al., "Changes in the Activity of Acetyl–CoA Carboxylase during Rape–Seed Formation," *Biochem. J.* 212:223–229 (1983).

Yanai, Y. et al., "RFLP Mapping of an Arabidopsis Acetyl–CoA Carboxylase," American Society of Plant Physiologists 1993 Annual Meeting, *Plant Physiol.* 102:S–70 (1993) (Abstract 382).

Goodwin, T.W. et al., "Introduction to Plant Biochemistry," Ed. 2, Pergamon Press, New York, p. 545 (1983).

Joshi, C.P., "An Inspection of the Domain Between Putative TATA Box and Translation Start Site in 79 Plant Genes," *Nucleic. Acids Res.* 15:6643–6653 (1987).

Nikolau, B.J. et al., "The Biochemistry and Molecular Biology of Acetyl–CoA Carboxylase and Other Biotin Enzymes," In N Murata, C Somerville, eds, Biochemistry and Molecular Biology of Membrane and Storage Lipids of Plants. American Society of Plant Physiologists, Rockville, MD, pp. 138–149 (1993).

Ohlrogge, J. et al., "Regulation of FLux Through the Fatty Acid Biosynthesis Pathway," In N. Murata, C Somerville eds, Biochemistry and molecular biology of membrane and storage lipids of plants. American Society of Plant Physiologists, Rockville, MD, pp. 102–112 (1993).

Kridl et al 1993 In Control of Plant Gene Expression; (Verma, eds); CRC Press, pp. 481–498.

Töpfer et al 1994 J. Plant Physiol. 143: 416–423.

```
Ara  MAGSV---NGNHSAVGPGINYETVSQYDEFCKALRGKRPIHSLLIANNGMAAVKFIRSVRTWAYETFGTEKALILVGMATPEDMRINAEHIRIADQFVEVPGGTNMNYANVQLIVEMAEV  118
Alf  ..-..GRG..YLNS.L.SRHPA.TTE...Y.N..G.NK............................S......................A.......................L.I..I

Ara  TRVDAVWPGWGHASENPELPDALDAKGIIFLGPPASSMAALGDKIGSSLIAQAADVPTLPWSGSHVKIPPNSNLVTIPEEIYRQACVTTEEAIASCQVVGYPAMIKASWGGGGKGIRKV  238
Alf  ......H..........................K....V......I.................E......................E.D.I...D....A...................

Ara  HNDDEVRALFKQVQGEVPGSPIFIMKVASQSRHLEVQLLCDKHGNVSALHSRDCSVQRRHQKIIEEGPITVAPPETVKKLEQAARRLAKSVNYVGAATIEYLYSMDTGEYYFLELANPRLQ  358
Alf  ..........................E.....................................I..Q....FA.........E.................Q...FA..........

Ara  VEHPVTEWIAEINLPAAQVAVGMGIPLMQIPEIRRFYGIEHGGGYDSWRKTSVVAFPFDFDKAQSIRPKGHCVAVRVTSEDPDDGFKPTSGRVQELSFKSKPNVWAYFSVKSGGGIHEFS  478
Alf  ........................................M......N.G.K....L.T....E....TK.............T.G.K.........................

Ara  DSQPGHVFAFGESRALALAIANMVLGLKEIQIRGEIRTNVDYTIDLLHASDYRDNKIHTGWLLDSRIAMRVRAERPPWYLSVVGGALYKASATSAAVVSDYVGYLEKGQIPPKHISLVHSQVS  598
Alf  ....................................................N......................................S...L...................

Ara  LNIEGSKYTIDVVRGGSGTYRLRMNKSEVVAEIHTLRDGGLLMQLDGKSHVIYAEEEAAGTRLLIDGRTCLLQNDHDPSKLMAETPCKLMRYLISDNSNIDADTPYAEVEVMKMCMPLLS  718
Alf  .S..........M...P.S.K.KL.Q..IE............................N..........................D.....IG......L...VA.D.Q.....

Ara  PASGVIHFKMSEGQAMQAGELIANLDLDDPSAVRKAEFPHGSFPPRLGLPTAISGRVHQRCAATLNAARMILAGYEHKVDE-VVQDLLNCLDSPELPFLQWQECFAVLATRLPKNLRNMLE  837
Alf  ....I....R.A.......K....G.......T....I.P....K..K..S.................NI..V..KS............................D...E..

Ara  SKYREFESISRNSLTTDFPAKLLKGILEAHLSSCDEKERGALERLIEPLMSLAKSYEGGRESHARVIVHSLFEEYLSVEELFNDNMLADVIERMRQLYKKDLLKIVDLVLSHQGIKNKNK  957
Alf  A..K..I..-S.Q.I.......A........P.N.K......V..T.V.........HK..Q........S..IQ......L.LQ........V.S.........

Ara  LVLRLMEQLVYPNPAAYRDKLIRFSTLNHTNYSELALKASQLLEQTKLSELRSNIARSLSELEMFTEDGENMDTPKRKSAINERIEDIVSASLAVEDALVGLFDHSDETLQRRVVETYIR  1077
Alf  .I....DK...........Q.....Q....I................S........................I.............D.M......P.........

Ara  RLYQPYVVKDSVRMQWHRSGLLASWEFLEEHMERKNIGLDDPDTSERGLVEKRSKRKWGAMVIIKSLQFLPSIISAALRETKHN-----DYETAGAPLSGNMMHIAIVGINNQMSLLQDS  1192
Alf  ......L....I......I.T......YV....-----.T.....H.EK..V..V......A........ATNFHDPLKSGSGDSSNH........GL........
```

STRUCTURE AND EXPRESSION OF AN ARABIDOPSIS ACETYL-COENZYME A CARBOXYLASE GENE

This is a continuation of U.S. patent application Ser. No. 08/248,630, filed May 24, 1994, now abandoned.

Work on this invention was sponsored in part by National Science Foundation Grant DCB 90-05290 and the Midwest Plant Biotechnology Consortium. The Government may have certain rights in the invention.

FIELD OF THE INVENTION

The present invention relates generally to an Arabidopsis acetyl-CoA carboxylase and more particularly, an acetyl-CoA carboxylase gene and its use in controlling the carboxylation of acetyl-CoA.

| GENBANK ACCESSION INFORMATION | |
|---|---|
| GENE | ACCESSION NO. |
| Arabidopsis ACCase | L27074 |

BIOLOGICAL DEPOSITS

The following Table sets forth the deposits made with the American Type Culture Collection (ATCC), 12301 Parklawn Drive, Rockville, Md. 20852, under the terms of the Budapest Treaty and accorded ATCC Accession No.:

| Subclone Name | Nucleotide Position | ATCC Accession No. | Date of Deposit |
|---|---|---|---|
| ACCA | Start codon to 1509 (plus adjacent 5' region) | 75760 | April 28, 1994 |
| ACCB | 1059 to 2825 | 75761 | April 28, 1994 |
| ACCC | 2825 to 5797 | 75762 | April 28, 1994 |
| ACCD | 5797 to 9142 | 75763 | April 28, 1994 |
| ACCE | 9142 to stop codon (plus adjacent 3' region) | 75764 | April 28, 1994 |

BACKGROUND OF THE INVENTION

Acetyl-CoA carboxylase (ACCase, EC 6.4.1.2) catalyzes the ATP-dependent carboxylation of acetyl-CoA to produce malonyl-CoA. This reaction occurs in two steps, carboxylation of a biotin prosthetic group using $HCO_3$ as a carboxyl donor, followed by a transfer of the carboxyl group from biotin to acetyl-CoA. The biotin carboxylase, carboxyl transferase, and biotin components of ACCase are each associated with different polypeptides in prokaryotes. Samols, D. et al., *J. Biol. Chem.* 263:6461–6464 (1988). In contrast, ACCase of non-plant eukaryotes is comprised of multimers of a single multi-functional polypeptide. In plants, evidence for both prokaryotic type ACCase (Kannangara, C. G. et al., *Arch. Biochem. Biophys.* 152:83–91 (1972); Nikolau, B. J. et al., "The Biochemistry and Molecular Biology of Acetyl-CoA Carboxylase and Other Biotin Enzymes," In N Murata, C Somerville, eds, *Biochemistry and Molecular Biology of Membrane and Storage Lipids of Plants*, American Society of Plant Physiologists, Rockville, Md. pp. 138–149 (1993) and Sasaki, Y. et al., *J. Biol. Chem.* 268:25118–25123 (1993)) and a eukaryotic type (Harwood, J. L., *Annu. Rev. Plant Physiol. Plant Mol. Biol.* 39:101–138 (1988)) has been obtained.

The malonyl-CoA produced by ACCase is used in a wide variety of reactions and pathways in plants, including fatty acid synthesis and elongation (Harwood, J. L., *Annu. Rev. Plant Physiol. Plant Mol. Biol.* 39:101–138 (1988)), flavonoid synthesis (Ebel, J. et al., *Eur. J Biochem.* 75:201–209 (1977) and Ebel, J. et al., *Arch. Biochem. Biophys.* 232:240–248 (1984)), malonation of the ethylene precursor aminocyclopropane-1-carboxylate (Liu, Y. et al., *Planta* 158:437–441 (1983); Kionka, C. et al., *Planta* 162:226–235 (1984)) and malonation of amino acids and glycosides. Malonyl-CoA must be available in multiple subcellular locations because some of these reactions such as fatty acid synthesis, occur in the plastid while others, such as flavonoid synthesis and fatty acid elongation, occur outside the plastid. For example, very long chain fatty acids are components of plasma membrane lipids (Cahoon, E. B. et al., *Plant Physiol.* 95:58–68 (1991)) and are also needed for synthesis of cuticular waxes to cover the surface of both aerial and underground tissues. Harwood, J. L., *Annu. Rev. Plant Physiol. Plant Mol. Biol.* 39:101–138 (1988). These very long chain fatty acids are synthesized outside the plastid by elongation of 16 or 18 carbon fatty acids exported from the plastid. Malonyl-CoA for the elongation reactions must be present in the cytosol, and is presumably provided by a cytosolic ACCase.

Malonyl-CoA must also be available in greatly differing amounts with respect to time and tissue. For example, increased amounts of malonyl-CoA are needed for fatty acid synthesis in developing seeds of species which store large quantities of triacylglycerols. Post-Beitenmiller, D. et al., "Regulation of Plant Lipid Biosynthesis: An Example of Developmental Regulation Superimposed on a Ubiquitous Pathway," In DPS Verma, ed, Control of Plant Gene Expression, CRC press, Boca Raton, Fla. pp. 157–174 (1993). In floral tissue, malonyl-CoA is used in the chalcone synthase reaction for synthesis of the flavonoid pigments which constitute up to 15% of the dry weight of this tissue. Goodwin, T. W. et al., "Introduction to Plant Biochemistry," 2nd ed., Pergamon Press New York, p. 545 (1983). In some tissues, ACCase might provide malonyl-CoA constitutively to produce fatty acids for membrane synthesis and maintenance, while providing a "burst" of malonyl-CoA for only a short period to synthesize flavonoids during exposure to UV light (Ebel, J. et al., *Eur J Biochem.* 75:201–209 (1977)) or during fungal pathogen attack. Ebel, J. et al., *Arch. Biochem. Biophys.* 232:240–248 (1984).

Various observations have led to the belief that ACCase is the rate-limiting enzyme for oilseed fatty acid synthesis. Analysis of substrate and product pool sizes has implicated ACCase in the light/dark regulation of fatty acid synthesis in spinach leaves and chloroplasts. Post-Beitenmiller, D. et al., *J. Biol. Chem.* 266:1858–1865 (1991) and Post-Beitenmiller, D. et al., *Plant Physiol.* 100:923–930 (1992). ACCase may also be the site of feedback inhibition of fatty acid synthesis in tobacco suspension cells supplemented with exogenous fatty acids. Shintani, D. K. et al., *Plant Physiol.* 102:S-11 (1993). Furthermore, ACCase activity increases in association with lipid deposition in developing seeds of oilseed crops. Simcox, P. D. et al., *Canada J. Bot.* 57:1008–1014 (1979); Turnham, E. et al., *Biochem. J.* 212:223–229 (1983); Charles et al., *Phytochem.* 25:55–59 (1986) and Deerburg, S. et al, *Planta* 180:440–444 (1990). ACCase therefore appears to have a very important regulatory role in plant fatty acid synthesis.

It would thus be desirable to provide a gene encoding acetyl-CoA carboxylase (ACCase). It would also be desirable to control the carboxylation of acetyl-CoA to produce malonyl-CoA. It would further be desirable to control the carboxylation of acetyl-CoA to produce malonyl-CoA by controlling the expression of a gene encoding ACCase. It would further be desirable to acquire long-term control of the carboxylation of acetyl-CoA to produce malonyl-CoA by genetically altering plants. It would also be desirable to control fatty acid synthesis and elongation in plants and seeds by controlling the expression of a gene encoding ACCase. It would further be desirable to control fatty acid synthesis and elongation in plants and seeds without employing foreign chemicals. It would also be desirable to control the production of plant secondary metabolites.

SUMMARY OF THE INVENTION

An Arabidopsis acetyl-CoA carboxylase (ACCase) gene has been isolated and sequenced. The 10 kb gene encodes a 251 kD cytosolic ACCase isozyme. The nucleic acid sequence of the gene is set forth in SEQ ID No. 1 and the gene has been accorded GenBank Accession No. L27074. Applicants have made a deposit of the entire Arabidopsis acetyl Co-A carboxylase gene divided into five SacI subclones in pBluescript KS+, with the American Type Culture Collection (ATCC), 12301 Parklawn Drive, Rockville, Md. 20852, under the terms of the Budapest Treaty. The five plasmid deposits have all been accorded an acceptance date of Apr. 28, 1994. The subclones are named ACCA, ACCB, ACCC, ACCD and ACCE, and accorded ATCC Acession Nos. 75760, 75761, 75762, 75763 and 75764, respectively. ACCA includes the SacI fragment from the start codon to nucleotide position 1509 of the ACCase gene, plus the adjacent 5' region. ACCB includes the SacI fragment from nucleotide position 1509 to 2825 of the ACCase gene. ACCC includes the SacI fragment from nucleotide position 2825 to 5797 of the ACCase gene. ACCD includes the SacI fragment from nucleotide position 5797 to 9142 of the ACCase gene. ACCE includes the SacI fragment from nucleotide position 9142 to the stop codon of the ACCase gene, plus the adjacent 3' region. Samples of the deposited material will be made available to the public upon issuance of a U.S. patent based on the present specification. The deposits will be maintained without restriction in the ATCC depository, which is a public depository, for a period of 30 years, or 5 years after the most recent request, or for the effective life of the patent, whichever is longer, and will be replaced if the deposits become depleted or nonviable during that period.

The cDNA of the Arabidopsis ACCase gene and deduced amino acid sequence of the cDNA are set forth in SEQ ID Nos. 2 and 3, respectively. By controlling expression of the gene of the present invention, carboxylation of acetyl-CoA to produce malonyl-CoA may be controlled. Thus, by introducing constructs of the gene of the present invention in sense or anti-sense orientation, carboxylation of acetyl-CoA to produce malonyl-CoA may be increased or decreased. Consequently, fatty acid synthesis and elongation in plants and seeds which is dependent on malonyl-CoA may also be controlled. Secondary metabolite production in plants which is also dependent on acetyl-CoA and malonyl-CoA may also be controlled. Moreover, long-term control of the carboxylation of acetyl-CoA to produce malonyl-CoA may be obtained by genetically altering plants with the sequences of the present invention.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIGS. 2A and 2B set forth the amino acid sequences of the Arabidopsis ACCase gene of the present invention compared to the alfalfa ACCase amino acid sequence;

FIG. 3 is a photograph of an Arabidopsis genomic DNA blot; and

FIG. 4 is a photograph of an RNase protection analysis of RNA from Arabidopsis tissues.

DESCRIPTION OF SEQUENCE LISTING

Figure 1:
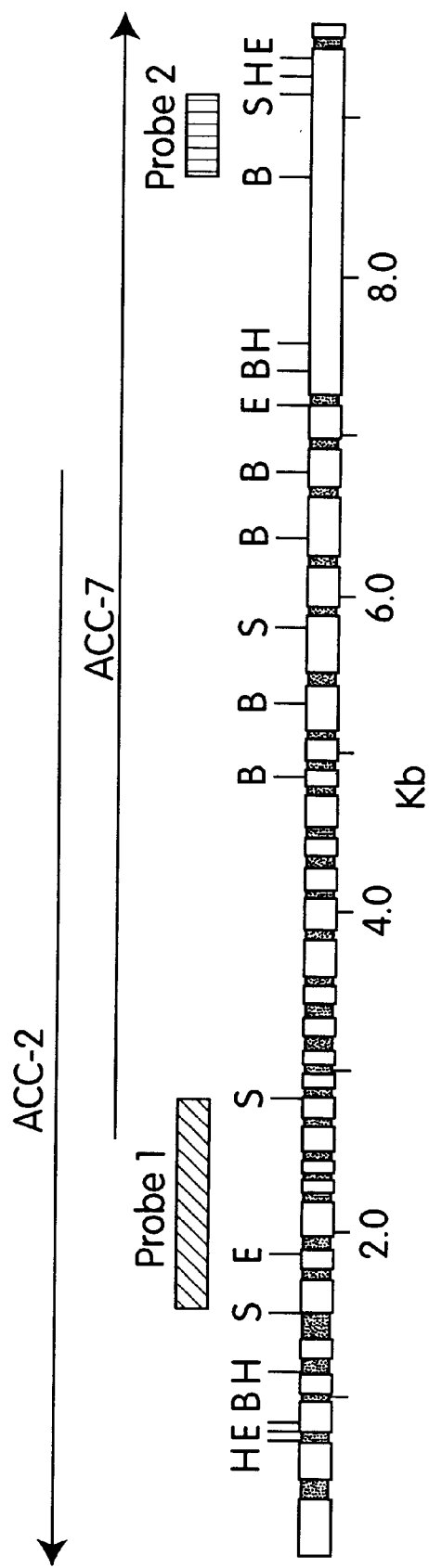
FIG. 1 is a map of the Arabidopsis ACCase gene of the present invention.

SEQ ID No. 1 is the nucleotide sequence of the genomic DNA of the Arabidopsis ACCase of the present invention.

SEQ ID No. 2 is the deduced cDNA of the Arabidopsis ACCase gene of the present invention.

SEQ ID No. 3 is the deduced amino acid sequence of the nucleotide sequence of Sequence SEQ ID No. 2.

DETAILED DESCRIPTION OF THE PREFERRED EMBODIMENTS

An Arabidopsis acetyl-CoA carboxylase (ACCase) gene has been isolated and sequenced, and the genomic DNA sequence is set forth in SEQ ID No. 1. The cDNA of the gene and deduced amino acid sequence of the cDNA are set forth in SEQ ID Nos. 2 and 3, respectively. It has been shown that the gene of the present invention is ubiquitously expressed, the gene product being found in diverse plant tissues. The sequences of the present invention may therefore be used to generally increase and decrease the carboxylation of acetyl-CoA to produce malonyl-CoA in plants. A method of controlling carboxylation of acetyl-CoA to produce malonyl-CoA is thus provided by the present invention.

The methods of the present invention generally comprise the step of introducing in sense or antisense orientation the ACCase gene described herein into a plant cell and growing the cell into a plant. The ACCase gene in sense or antisense orientation may be fused to a gene or fragment thereof which allows the ACCase gene to be transported and expressed in a plant cell. The ACCase gene in sense or anti-sense orientation in combination with the gene or gene fragment is referred to as a "construct" herein. It will be appreciated that the constructs of the present invention may contain any regulatory elements necessary and known to those skilled in the art for expression of the ACCase gene in either orientation. For example, constructs prepared with either seed-specific promoters such as the napin seed storage protein promoter of rapeseed, or with a constitutive promoter such as the cauliflower mosaic virus 35 S promoter, are contemplated by the present invention. Seed-specific promoters may be more desirable and effective in altering seed oil amounts or composition because possible deleterious effects in the plant may be avoided. The constitutive promoter, however, may be more effective in, for example, engineering general herbicide resistance in the whole plant.

Because malonyl-CoA is required for fatty acid synthesis and elongation in plants and seeds, the present invention also provides a method of controlling plant and seed fatty acid synthesis and elongation. Increasing seed fatty acid synthesis by overexpressing the ACCase gene is useful in increasing oil content of rapeseed, soybean, or other oilseed crops. Decreasing seed fatty acid synthesis by decreasing ACCase gene expression is also useful in producing "low-fat" seeds such as low-fat peanuts. Since fatty acid synthesis takes place primarily in the plastid, a construct which includes the cytosolic ACCase gene described herein in sense orientation, fused to a gene fragment encoding a plant plastid transit peptide is also provided by the present invention. This allows the ACCase polypeptide to be transported into the plastid. The cytosolic ACCase protein described herein may differ significantly from the endogenous plastid ACCase protein, and therefore may be less subject to endogenous regulatory controls. A more effective increase in ACCase activity in the plastid thus results when the cytosolic ACCase gene of the present invention is expressed, compared to overexpression of the authentic plastid ACCase gene.

Increasing seed fatty acid elongation by overexpressing the gene described herein is also useful in increasing the content of very long chain fatty acids such as erucic acid in the seed oil of rapeseed, Crambe, and other oilseed plants. This is desirable because erucic acid and its derivatives can be used in making lubricants, plasticizers and nylons, and has other industrial uses as well. Battey, J. F. et al., *Trends in Biotech.* 7:122–125 (1989). Although erucic acid has important industrial uses, it may not be healthy for human consumption in food products. Therefore, reducing fatty acid elongation, and thereby reducing erucic acid content, by decreasing the expression of cytosolic ACCase genes through anti-sense RNA methods, is also desirable. This may result in seed oil of rapeseed, mustard, Crambe and other oilseed plants that is suitable for human consumption because of the reduced content of erucic acid, eicosenoic acid and other very long chain fatty acids. In addition, anti-sense RNA approaches have been successful in reducing expression of heterologous genes that are substantially different from the gene in the construct. Salehuzzaman et al., *Plant Mol. Biol. Biol.* 23:947–962 (1993). Therefore, an anti-sense RNA construct prepared with the Arabidopsis gene described herein may be useful in decreasing expression of ACCase genes from plant species other than Arabidopsis.

ACCase is also the target for herbicides of the aryloxyphenoxy propionate and cyclohexanedione families. Burton, J. D. et al., *Biochem. Biophys. Res. Commun.* 148:1039–1044 (1987). The ACCase of some monocots such as corn is far more susceptible to these herbicides than is the ACCase of dicot species. Therefore, overexpression of the ACCase gene of the present invention from the dicot Arabidopsis in plastids of susceptible species like corn, may result in herbicide resistance in the desired species. Herbicides would thus be useful in controlling monocot weeds in fields of the genetically engineered plant species.

As previously discussed, acetyl-CoA and malonyl-CoA are precursors of various plant secondary metabolites. Thus, increasing expression of the ACCase gene of the present invention increases the amount of malonyl-CoA available for synthesis of flavonoids, isoflavonoids, and other secondary metabolites. Conversely, decreasing expression of the ACCase gene of the present invention may decrease the amount of malonyl-CoA present and increase the amount of acetyl-CoA present. Thus, altering expression of the ACCase gene of the present invention could favorably alter the amount of acetyl-CoA or malonyl-CoA available for production of secondary plant products, many of which have value in plant protection against pathogens, or for medicinal or other uses. Furthermore, it is not necessary that these products be naturally present in plants. For example, bacterial genes may be introduced into plants to produce polyhydroxybutyrate which can be used to synthesize biodegradable plastics. Poirier Y. et al., *Science* 256:520–524 (1992). Since acetyl-CoA is a precursor for this product, increasing the acetyl-CoA to malonyl-CoA ratio by decreasing ACCase gene expression may allow more carbon flux into polyhydroxybutyrate production thereby resulting in higher yields of polyhydroxybutyrate.

It will be appreciated that the methods of the present invention further include introducing the constructs of the present invention including the sense or antisense orientation of the gene of the present invention, into a plant cell, and growing the cell into a callus and then into a plant; or, alternatively, breeding a transgenic plant produced from the above method with a second plant to form an F1 or higher hybrid (e.g. F2). Transgenic plants are therefore produced by the methods of the present invention and are also contemplated by the present invention.

As referred to herein, the term "gene" is meant a nucleic acid, either genomic or synthetic, which encodes a protein product. The term "nucleic acid" is intended to mean natural and synthetic linear and sequential arrays of nucleotides and nucleosides, e.g. in cDNA, genomic DNA (gDNA), mRNA, and RNA, oligonucleotides, oligonucleosides, and derivatives thereof. The term "sense orientation" as used herein refers to the orientation of a gene such that its RNA transcript, following removal of introns, is translatable into the polypeptide product of the gene. The term "antisense orientation" is used to mean the opposite orientation of a gene such that its transcript is complementary to the normal transcript of the gene when in sense orientation. In addition, the term "encoding" is intended to mean that the subject nucleic acid may be transcribed and translated into either the desired polypeptide or the subject protein in an appropriate expression system, e.g. when the subject nucleic acid is linked to appropriate control sequences such as promoter and enhancer elements in a suitable vector (e.g. an expression vector) and when the vector is introduced into an appropriate system or cell. It will thus be appreciated that the present invention includes vectors comprising the sequences of the present invention.

By "substantially represented by" or "substantially complementary to" as used herein is meant any variation therein does not impair the funtionability of the sequence to any significant degree. By "substantially as shown" or "substantially similar" with respect to a nucleic acid is meant sufficiently similar in structure or sequence to encode the desired polypeptide or gene product, or with respect to a polypeptide, sufficiently similar in structure or sequence to serve its principal function. The terms "oilseed plant" and "oilseed crop" are used interchangeably herein and refer to those plants and crops known to those skilled in the art as part of the oilseed variety, including but not limited to rapeseed, soybean, Crambe, mustard, castor bean, peanut, sesame, cottonseed, linseed, sunflower and gold of pleasure.

The term "capable of hybridizing under stringent conditions" is used to mean annealing a first nucleic acid to a second nucleic acid under stringent conditions (defined below). For example, the first nucleic acid may be a test sample, and the second nucleic acid may be a portion of the nucleic acid sequence set forth in SEQ ID No. 1. Hybridization of the first and second nucleic acids is conducted under stringent conditions, e.g., high temperature and/or low salt content, which tend to disfavor hybridization of dissimilar nucleotide sequences. A suitable protocol involves hybridization in 5 X SSC, at 65° C. in aqueous solution or 42° C. in formamide, followed by washing with 0.1 X SSC, at 65° C. in aqueous solution. (Other experimental conditions for controlling stringency are described in Maniatis, T., et al., *Molecular Cloning; A Laboratory Manual*, Cold Springs Harbor Laboratory, Cold Springs, N.Y., 1982, at pages 387–389; and also in Sambrook, J. et al., *Molecular Cloning; A Laboratory Manual, Second Edition*, Volume 2, Cold Springs Harbor Laboratory, Cold Springs, N.Y., at pages 8.46–8.47 (1989)). It will be appreciated, however, that although reference herein is made to nucleic acids capable of hybridizing under stringent conditions, hybridization in the practice of the present invention need not actually be conducted under such conditions.

The following Specific Example and Discussion further explains the present invention.

SPECIFIC EXAMPLE I

Materials and Methods

Isolation and Sequence Analysis of Genomic Clones. To obtain an ACCase probe, polymerase chain reaction (PCR) was carried out with a coriander endosperm cDNA library (Cahoon, 1993). Degenerate primers were prepared to two peptides conserved in ACCase of rat, chicken and Cyclotella: VEIKFR and FADLHD, corresponding to residues 2038 to 2043 and 2102 to 2107 of FIG. 2B. A 207 bp PCR product with identity to known ACCase sequences was obtained and used to screen an *Arabidopsis thaliana* Ecotype Columbia λgem 11 genomic library (provided by Carrie Schnieder and Chris Somerville of the Camagie Institute of Washington, Standford, Calif.). One positive clone was obtained by screening 1.6 X $10^5$ plaques. A restriction fragment of this clone was used to reprobe the same filters and four additional positive clones were obtained. The same genomic library was subsequently screened with a restriction fragment of an alfalfa ACCase cDNA (Shorrosh, B. S. et al., *PNAS (USA)* (in press) (1994)) and six more positive clones were obtained. Restriction mapping plus partial sequence analysis of overlapping regions revealed that these 11 clones all represented the same gene and that none contained the entire ACCase coding region (not shown). Two overlapping clones (ACC-2 and ACC-7 of FIG. 1) were then sequenced extensively to determine the coding region. All of the coding region included in ACC-7 was sequenced, and the remainder of the coding region was obtained from ACC-2. Both strands of the coding region were sequenced in entirety as subcones in pBluescript KS$^+$ (Stratagene) using either dideoxy chain termination with the Sequence kit (U.S. Biochemical) or a dye-primer method through the Michigan State University sequencing facility.

cDNA Synthesis. To confirm the identity of the ACCase start methionine, a cDNA which included the surrounding region was synthesized and sequenced. First strand cDNA was synthesized with Moloney Murine leukemia virus reverse transcriptase using five μg Arabidopsis total RNA and a 17-mer primer (JO177) corresponding to the region encoding asparagine 354 to valine 359 of FIG. 2A. Double stranded cDNA was then synthesized by PCR with the first stand cDNA as template, using JO177 and a primer (JO190) from the 5' non-translated region of the ACCase gene. An aliquot of this PCR product was used in a second round of PCR with JP190 and a 3' primer (JO191) corresponding to the region encoding leucine 177 to serine 182 of FIG. 2A. First strand cDNA synthesis and PCR reactions were done under conditions similar to those described in Shorrosh, B.

S. et al., *PNAS (USA)* (in press) (1994). The resulting PCR product was sequenced and found to be identical to the corresponding genomic DNA sequence except that the first intron of FIG. 2A was missing in the cDNA sequence as expected. In both the genomic DNA and cDNA sequences, an in-frame stop codon was observed 15 bp upstream from the start methionine of FIG. 2A.

Genomic DNA Blot Analysis. Ten μg of Arabidopsis genomic DNA were digested with Bg/II, EcoRI, HindIII, or SacI, electrophoresed in a 0.8% agarose gel and blotted to Zetaprobe nylon membrane (Biorad) in 0.4 N NaOH. The probe was a random hexamer-labelled 1316 bp SacI fragment of the ACCase gene (probe 1 of FIG. 1). Hybridization was carried out in 5 X SSC, 0.05 X blotto (Sambrook, J. et al., *Molecular Cloning. A Laboratory Manual*, Ed2. Cold Springs Harbor Laboratory Press, Cold Springs Harbor, N.Y. (1989)) at 55° C. for 16 hours. The blot was washed twice for 30 minutes each in 0.2 X SSC, 0.1% SDS at 55° C.

RNase Protection Analysis. Plasmid pBluescript KS$^+$ containing a 3345 bp SacI fragment of the ACCase gene was linearized with Bg/II and a 643 nucleotide $^{32}$P-labelled RNA probe was synthesized with T3 polymerase using the materials and procedure of a Maxiscript kit (Ambion). The RNA probe contained 527 nucleotides from the ACCase gene (corresponding to probe 2 in FIG. 1). with the remainder from the vector polylinker. RNase protection assays were done using an RPA II kit (Ambion). The labelled RNA probe was hybridized at 45° C. for 16 hours with 5 μg of total RNA from Arabidopsis root, leaf, silique (including seed), or seed. Following hybridization, digestion with RNase A and T1 was done and labelled, protected RNA was resolved in a 5% polyacrylamide, 8M urea gel. Control assays were done with 10 μg each of Torulla yeast RNA, with or without the RNase digestion. The RNA was isolated from 5 to 7 week old Arabidopsis plants grown in soil in continuous light. The isolation procedure of Hall, T. C. et al., *PNAS (USA)* 75:3196–3200 (1978) was followed except that developing seed was homogenized in a microfuge tube with a minipestle.

Results

Figure 2B:
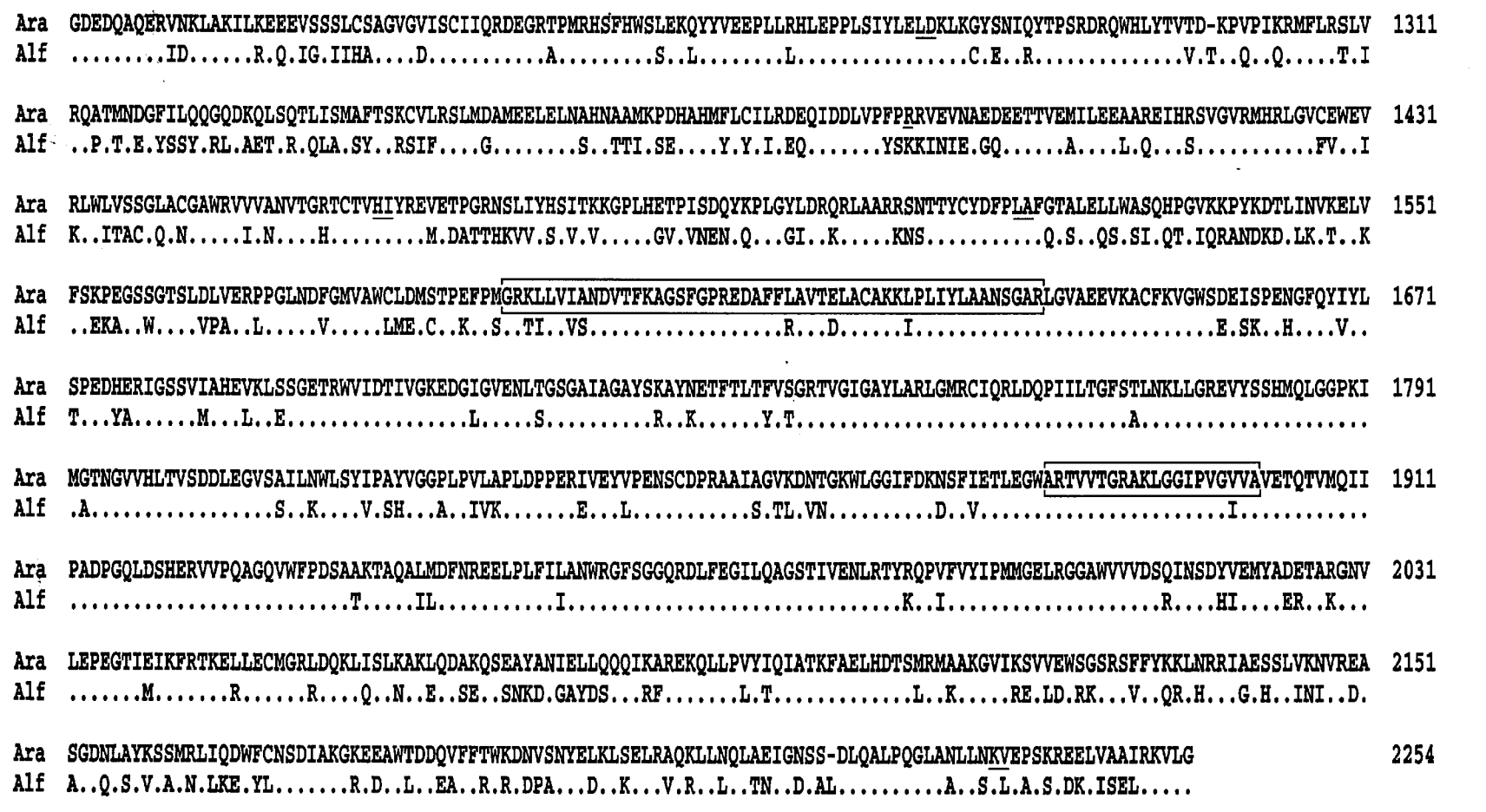

ACCase Sequence Characterization. Eleven Arabidopsis ACCase clones were obtained by screening a genomic library with a coriander ACCase PCR product or by screening with a restriction fragment of an alfalfa ACCase cDNA. Two overlapping clones ACC-2 and ACC-7 were sequenced to determine the entire ACCase coding region, as shown in FIGS. 1, 2A and 2B. In FIG. 1, introns are shown as solid bars and the following letters represent sites of restriction enzymes used in DNA blot analysis: B=Bg/II, E=EcoRI, H=HindIII and S=SacI. Probes 1 and 2 shown in FIG. 1, were used in genomic DNA blot analysis and in RNase protection assays, respectively. The nucleic acid sequence of the gene is set forth in SEQ ID No. 1. The deduced cDNA of the gene is set forth in SEQ ID No. 2 and the deduced amino acid sequence of the cDNA is set forth in SEQ ID No. 3.

To ensure that these clones represented the same gene, 940 bp of the overlapping region, including 4 introns, were sequenced from both clones and found to be identical. Thirty introns were identified by comparing the Arabidopsis gene with an alfalfa ACCase cDNA sequence, which is shown in FIGS. 2A and 2B. In FIGS. 2A and 2B, the alfalfa sequence (Shorrosh, B. S. et al., *PNAS (USA)* (in press) (1994)) is shown only where different from Arabidopsis. Adjacent underlined residues indicate an intron located between codons. Single underlined residues indicate an intron located within a codon.

As shown in FIGS. 2A and 2B, the Arabidopsis ACCase amino acid sequence was identical to the alfalfa sequence across most introns. Furthermore, the exon/intron border junctions fit the consensus sequence n/gt . . . ag/n (Goodall, G. J. et al., *EMBO J.* 10:2635–2644 (1991)) for 29 or 30 introns. The remaining intron, the 15th from the 5'0 end, used gc rather than gt at the 5' junction. This border sequence, though rare, has been observed previously in other Arabidopsis introns, evident from a table of 569 Arabidopsis introns as compiled by Mike Cherry and posted in Arabidopsis E-mail network, Sep. 13, 1993. The introns ranged in size from 73 bp to 180 bp and averaged 94 bp.

The Arabidopsis ACCase gene encoded a 2254 amino acid polypeptide with a calculated molecular mass of 251 kd and a pI of 6.0. In several previous studies, ACCase purified from plants comprised a homodimer of >200 kD subunits (Egin-Buhler, B. et al., *Eur. J Biochem.* 133:335–339 (1983)), consistent with the deduced molecular mass of the Arabidopsis polypeptide determined here. Biotin is covalently bound to a lysine residue flanked by methionine residues in most biotin-containing polypeptides so far sequenced. This MKM consensus sequence was identified in Arabidopsis ACCase at residues 710 to 712. As shown in FIG. 2A, the asterik at position 711 marks the biotin binding site. Proline residues were observed 27 to 35 positions upstream from this biotin binding site, similar to previous observations with ACCase of other eukaryotes. These double proline residues are proposed to form a hinge which allows the $HCO_3^-$ binding site to approach the biotin binding site, thus facilitating carboxyl transfer. Samols, D. et al., *J Biol. Chem.* 263:6461–6464 (1988). Regions of the ACCase primary structure proposed to be involved in the binding of ATP, carboxybiotin, and acetyl-CoA (Al-Feel, W. et al., *PNAS (USA)* 89:4534–4538 (1992); Li, S-J. et al., *J Biol. Chem.* 267:855–863 (1992) and Li, S-J. et al., *J. Biol. Chem.* 267:16841–16847 (1992)) were also located in the Arabidopsis sequence. The proposed ATP, carboxybiotin and acetyl-CoA binding sites are shown, respectively, as three boxed regions from N-terminus to C-terminus, in FIGS. 2A and 2B. The start methionine shown in FIG. 2A was initially identified based on its surrounding nucleotide sequence (ACAATGGCT) which fit the consensus sequence for higher plant start methionines. Joshi, C. P., *Nucleic Acids Res.* 15:6643–6653 (1987) and Lutcke, H.A. et al., *EMBO J.* 6:43–48 (1987). Sequencing 560 bp upstream revealed no other methionines which conformed well to the consensus sequence. To confirm the identity of the start methionine, a cDNA which included the surrounding region was synthesized and sequenced. An in-frame stop codon was observed 15 bp upstream from the start methionine in both the genomic and cDNA sequences. The position of the start methionine is conserved with that of the alfalfa ACCase start methionine which is also known to be authentic because of in-frame upstream stop condons in the cDNA sequence. Shorrosh, B. S. et al., *PNAS (USA)* (in press) (1994). Features of higher plant chloroplast transit peptides (Keegstra, K. et al., *Annu. Rev. Plant Physiol. Plant Mol. BioL* 40:471–501 (1989)) were not evident in the Arabidopsis sequence. Acidic residues, rare in transit peptides, were observed at positions 19, 25 and 26. Sequence identity with cytosolic ACCase of chicken and rat was observed as near as 20 residues from the start methionine, with too few residues remaining to comprise a typical transit peptide of 30 to 70 residues. Other characteristics of transit peptides, such as very abundant serine and threonine residues, were also absent.

The Arabidopsis ACCase amino acid sequence was compared with ACCase sequences of diverse organisms, including alfalfa (Shorrosh, B. S. etal., *PNAS (USA)* (in press) (1994)), yeast (Al-Feel, W. et al., *PNAS (USA)* 89:45344538 (1992)), rat (Lopez-Casillas, F. et al., *PNAS (USA)* 85:5784–5788 (1988)), chicken (Takai, T. et al., *J. Biol. Chem.* 263:2651–2657 (1988)) and Cyclotella (Roessler, P. G. et al., *J. Biol. Chem.* 268:19254–19259 (1993)). The GCG Gap program (Devereux, J. etal., *Nucleic Acids Res.* 12:387–395 (1984)) was used with values of 5.0 and 0.3 for gap weight and gap length, respectively. As shown in Table 1 below, substantial identity was found in the N-terminal region containing the biotin carboxylase domain and the biotin binding site. Considerable identity was also observed in the C-terminal regions which includes the carboxyl transferase domain. In contrast, much less identity was found in the central third of the primary structure. Arabidopsis ACCase had 80% amino acid sequence identity overall in comparison with alfalfa ACCase, and about 40% identity with ACCase of rat, chicken, yeast and the alga Cyclotella. Rat liver ACCase is regulated by reversible phosphorylation. Kim, K-H. et al., *FASEB J.* 3:2250–2256 (1989). None of the 7 serine residues known to be phosphorylated in the rat enzyme are present in Arabidopsis ACCase.

TABLE 1

ACCase Amino Acid Sequence Comparisons

| | Arabidopsis ACCase Amino Acid | | | |
|---|---|---|---|---|
| Source | 1–762 | 763–1546 | 1547–2254 | Total |
| Alfalfa | 89% | 73% | 78% | 80% |
| Yeast | 50% | 27% | 48% | 42% |
| Rat | 51% | 25% | 47% | 41% |
| Chicken | 51% | 24% | 46% | 40% |
| Cytclotella | 47% | 21% | 46% | 39% |

Partial sequences of 1306 and 546 residues for maize and wheat ACCase are also available (Ashton et al., unpublished GenBank sequences S34636; S35959). These monocot ACCase sequences have 62% and 69% identity, respectively, with the corresponding regions of Arabidopsis ACCase. Over these same regions, alfalfa ACCase has 74% and 78% identity with the Arabidopsis enzyme.

Figure 3:
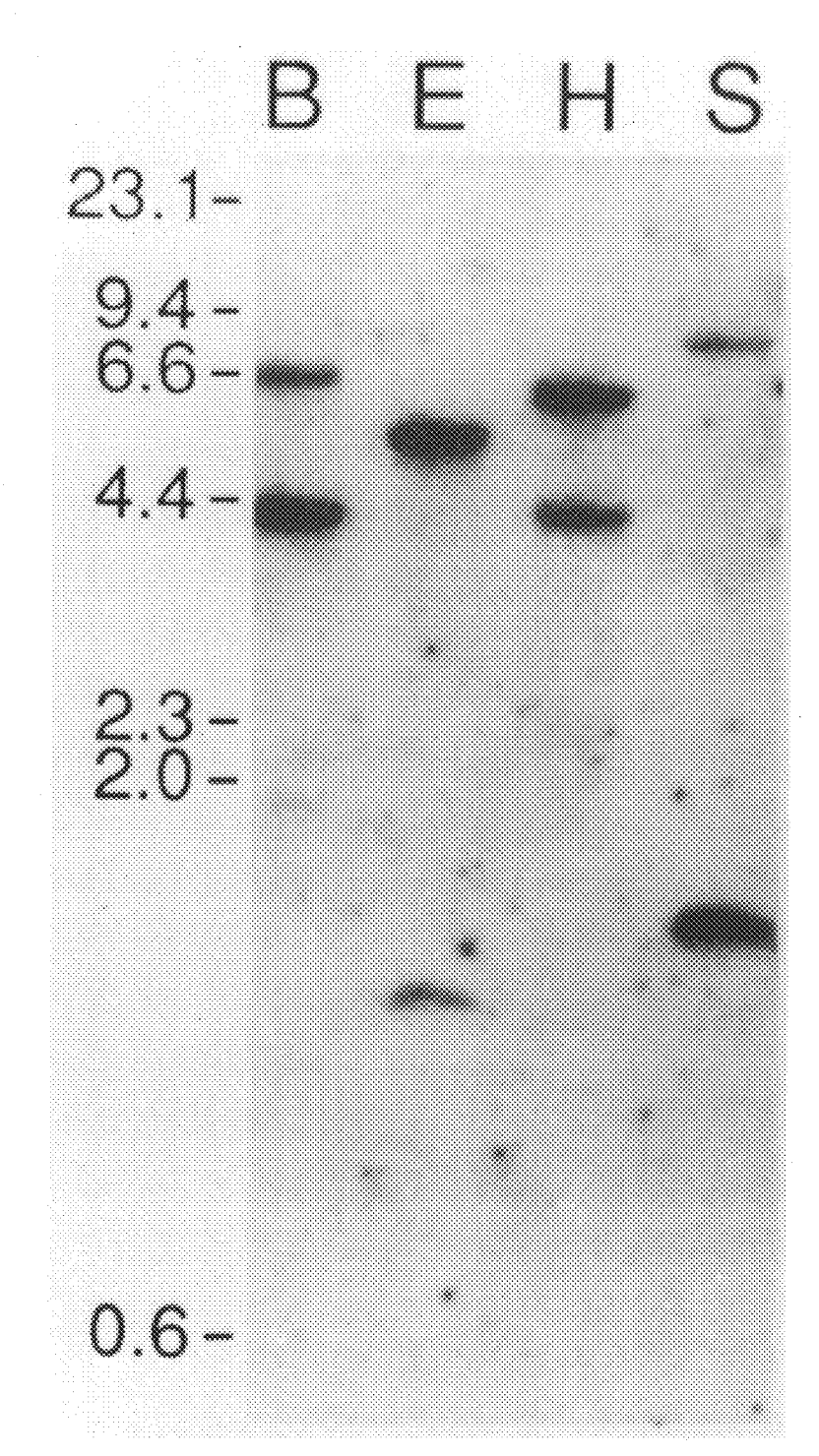

Genomic DNA Blot Analysis. An Arabidopsis genomic DNA blot was probed with a 1316 bp SacI fragment from the biotin carboxylase region of the ACCase gene, shown as probe 1 of FIG. 1. FIG. 3 is a photograph of the DNA blot. Restriction enzymes used were Bg/II, EcoRI, HindIII and SacI, shown as B, E, H and S, respectively, in FIG. 3. Approximate sizes in kb are given on the left of FIG. 3. As shown in FIG. 3, the probe contained one internal EcoRI site. Expected band(s) of the correct size were observed in each lane. In addition, a less prominent unexpected band was clearly visible in the Bg/II, Hind/III and SacI lanes, suggesting the presence of a second ACCase gene. With the HindIII digest, the second band was smaller in size than the expected band, thus ruling out any artifact resulting from a partial digest. To further confirm the presence of a second Arabidopsis ACCase gene, a second blot was prepared with the same restriction enzymes and probed with an 1152 bp Bg/I/SacI fragment from the carboxyl transferase region, corresponding to the region encoding serine 1585 to aspartate 1969 (see FIG. 2B). One extra band was again observed in some lanes (not shown), further suggesting the presence of a second gene. Similar evidence for two Arabidopsis ACCase genes has been obtained independently. Yanai, Y. et al., *Plant Physiol.* 102:S-70 (1993).

Figure 4:
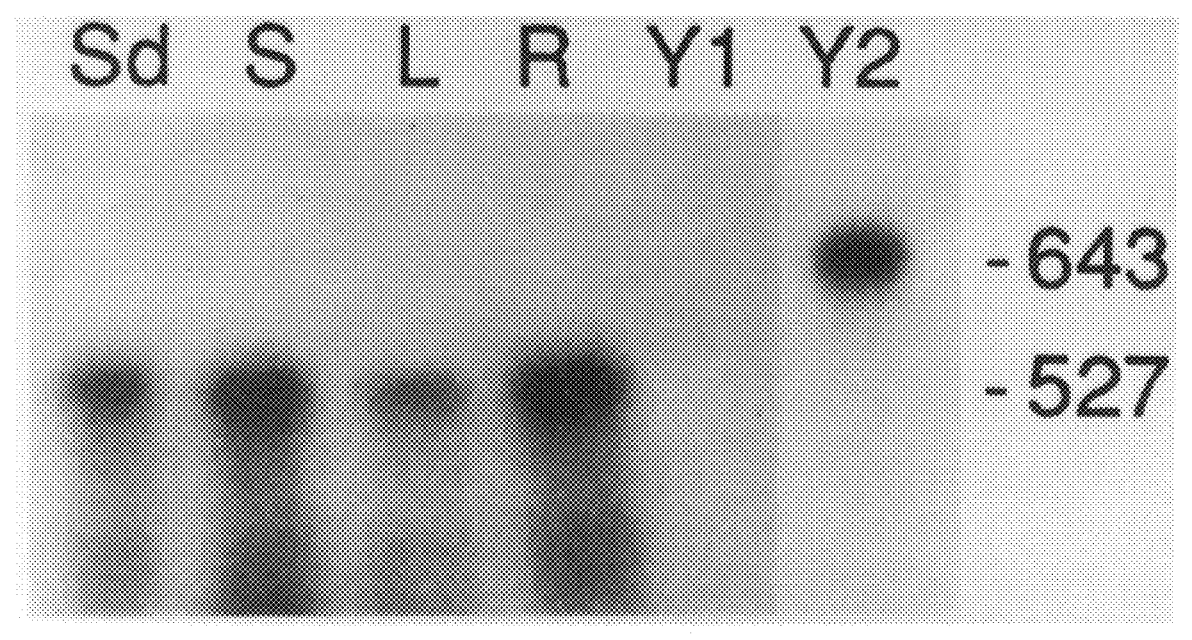

RNase Protection Assays. The presence of two cross-hybridizing Arabidopsis ACCase genes seemed likely to complicate RNA blot analysis. Therefore, RNase protection assays, rather than RNA blots were done to assess tissue-specific expression of the cloned ACCase gene. Only RNA transcripts from the cloned gene should be detected with this assay, since even single base mismatches in the hybrid would be cleaved during RNase treatment. Myers, R. M. et al., *Science* 230:1242–1246 (1985). FIG. 4 is a photograph of the RNase protection analysis.

The labelled RNA probe was from the carboxyl transferase region of the Arabidopsis ACCase gene, shown as probe 2 in FIG. 1. Controls were 10 µg of Torulla yeast RNA with (shown as Y1 in FIG. 4) or without (shown as Y2 in FIG. 4), the RNase treatment. Arabidopsis total RNA (5 µg) from root, leaf, silique or seed was used, represented as R, L, S and Sd, respectively, in FIG. 4. Film exposure times were 2 hours for Y2 and 6 days for all other samples. Sizes in nucelotides are shown on the right of FIG. 4.

As shown in FIG. 4, RNA from Arabidopsis root, leaf, silique and seed all showed protection by the ACCase probe. The protected fragment was smaller than the probe as expected, since the probe included additional sequence from the vector polylinker. The yeast control RNA showed no protection.

DISCUSSION

The studies described above provide two lines of evidence that multiple ACCase genes exist in Arabidopsis. First, the cloned Arabidopsis gene does not appear to have a transit peptide sequence, suggesting that it encodes a cytosolic ACCase isozyme. Because fatty acid synthesis occurs primarily in the plastid and isolated chloroplasts possess ACCase activity sufficient to support in vivo rates of fatty acid synthesis (Laing, W. A. et al., FEBS Lett. 144:341–344 (1982)) another gene(s) encoding a plastid ACCase isozyme must exist. Consistent with this expectation, ACCase has been partially purified from isolated plastids. Finlayson, S. A. et al., *Arch. Biochem Biophys.* 225:576–585 (1983). Second, the genomic DNA blot analysis suggests the presence of two related Arabidopsis ACCase genes. Whether the additional gene encodes a plastid ACCase isozyme, or rather another cytosolic isozyme is yet to be determined. The observation of multiple ACCase genes is consistent with previous biochemical studies. Two maize ACCase isozymes were purified, only one of which was detected in chloroplasts. Egli, M. A. et al., *Plant Physiol.* 101:499–506 (1993). It seems likely that the maize isozymes are encoded by two genes because polyclonal antibodies to one isozyme did not cross-react well with the other isozyme. Other possible explanations for the two maize isozymes, such as proteolytic processing of a single gene product, alternate splicing of RNA from the same gene, or use of alternate start condons to generate two polypeptides from the same gene would result in polypeptides sharing much structural identity, and substantial antibody cross-reactivity would thus have been observed. An ACCase complex of 91 kD, 87 kD and 35 kD subunits was recently proposed for pea chloroplasts. Sasaki, Y. et al., *J. Biol. Chem.* 268:25118–25123 (1993). If a similar complex is present in Arabidopsis, then additional genes besides the one described herein would be needed to encode the small polypeptides.

The Arabidopsis ACCase gene message was detected in all tissues examined, including both vegetative and reproductive tissues. This ubiquitous expression is not surprising considering the need for malonyl-CoA in the cytosol of all cells. As discussed in the Background, very long chain fatty acids are components of plasma membrane lipids (Cahoon, E. B. et al., *Plant Physiol.* 95:58–68 (1991)) and are also needed for synthesis of cuticular waxes to cover the surface of both aerial and underground tissues. Harwood, J. L., *Annu. Rev. Plant Physiol. Plant Mol. Biol.* 39:101–138 (1988). These very long chain fatty acids are synthesized outside the plastid by elongation of 16 or 18 carbon fatty acids exported from the plastid. Malonyl-CoA for the elongation reactions must be present in the cytosol, and is presumably provided by a cytosolic ACCase. Detection of the cytosolic ACCase gene message in developing seed is also reasonable because Arabidopsis, like numerous Brassicacea species, contains the very long chain fatty acids eicosenoic (20:1) and erucic (22:1) in seed storage triacylglycerols (James, D. W. et al., *Theor Appl. Genet* 80:241–245 (1990)), and these fatty acids are also synthesized by elongation of oleic acid exported from the plastid. Pollard, M. R. et al., *Plant Physiol.* 66:649–655 (1980). Anti-sense RNA experiments with tissue-specific promoters utilizing the sequences of the present invention, may further define the precise functions in each tissue for the cytosolic ACCase isozyme described herein. Somers, D. A. etal., *Plant Physiol.* 101:1097–1101 (1993) reported that one ACCase gene product was present in both leaf and seed in maize. It was the major ACCase isozyme in both tissues and was concluded to be involved in fatty acid biosynthesis for both membranes and seed embryo triacylglycerol. The maize gene of Sommers et al. therefore encodes a plastid ACCase isozyme and does not correspond to the cytosolic ACCase gene of the present invention.

The ubiquitous expression of the Arabidopsis ACCase gene of the present invention differs from that of an alfalfa cytosolic ACCase gene. The alfalfa gene message was not detected in alfalfa suspension culture cells except when induced with fungal elicitors. Shorrosh, B.S. et al., *PNAS (USA)* (in press) (1994). Perhaps the primary role of the alfalfa gene is to provide malonyl-CoA for isoflavonoid synthesis when needed for the plant defense system, and at other times this gene is not expressed. Alternatively, the alfalfa gene could be expressed in unelicited cells at a basal level too low to be readily detected by RNA blot analysis which is less sensitive than the RNase protection method decribed herein. Extensive analyses and comparisons of the promoters of these two genes may reveal differences that explain the different expression patterns.

The amino acid sequence comparisons revealed that Arabidopsis ACCase has lower sequence identity with wheat or maize ACCase than with alfalfa ACCase. Since the wheat and maize sequences are not complete, it can not be determined whether they represent plastid or cytosolic ACCase isozymes. Therefore it is not known if the lesser sequence identity reflects primarily differences between dicot versus monocot cytosolic ACCase, or rather reflects structural differences between plastid and cytosolic ACCase isozymes. Because of the different environments (e.g. different pH and [$Mg^{2+}$]) in the plastid versus the cytosol of plant cells, substantial structural differences in the isozymes from these locations might be expected.

As discussed above, ACCase has an important regulatory role in plant fatty acid synthesis and elongation. Thus, the ACCase gene described herein provides a basis to further examine plant and seed oil production, plant secondary metabolite production and herbicide resistance.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

All references referred to herein are incorporated by reference.

We claim:

1. An isolated nucleic acid comprising a nucleotide sequence encoding the Arabidosis cytosolic ACCase of SEQ ID No. 3.

2. A DNA construct comprising a nucleotide sequence encoding the polypeptide of SEQ ID No. 3 operatively-linked to a nucleotide sequence encoding a plastid transit peptide.

3. The DNA construct of claim 2 wherein the plastid transit peptide is a chloroplast transit peptide.

4. A vector comprising the DNA construct of claim 2.

5. A plant cell transformed with the vector of claim 4.

6. A plant transformed with the DNA construct of claim 2.

7. Seed of the plant of claim 6 comprising said DNA construct.

8. A DNA construct comprising a nucleotide sequence encoding a plant cytosolic acetyl-CoA carboxylase operatively-linked to a nucleotide sequence encoding a plastid transit peptide.

9. A plant transformed with a nucleic acid comprising a nucleotide sequence encoding the polypeptide of SEQ ID No. 3.

10. A vector comprising the DNA construct of claim 8.

11. A plant transformed with the vector of claim 10.

12. A plant transformed with the DNA construct of claim 8.

13. Seed of the plant of claim 12 comprising said DNA construct.

14. The DNA construct of claim 8, wherein the plastid transit peptide is a chloroplast transit peptide.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 9581 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:1:

```
ATGGCTGGCT CGGTTAACGG GAATCATAGT GCTGTAGGAC CTGGTATAAA TTATGAGACG      60

GTGTCTCAAG TGGATGAGTT CTGTAAAGCA CTTAGAGGGA AAAGGCCGAT CCATAGTATT     120

TTGATAGCTA ACAATGGAAT GGCGGCTGTG AAGTTTATAC GTAGTGTCAG AACATGGGCT     180

TATGAAACAT TTGGTACGGA AAAAGCCATA TTGTTGGTGG GGATGGCAAC CCCTGAAGAC     240

ATGCGGATCA ATGCGGAGCA TATCAGAATC GCTGATCAGT TTGTTGAGGT TCCCGGAGGA     300

ACCAACAATA ACAATTATGC TAACGTTCAG CTGATTGTGG AGGTGAATCC AACTTTTTGG     360

GAACTACTAT TATCTGAATT ATCGTGTTTT ACTGTACAGA ACACATGTAT TAAGCTCAAT     420

TTCAGCAATG AAGTTTTGGT CTTTGGAGTT ATTTTTCATT CATCTGAACA TCTTTGTCTA     480

CAACCTGTGT GCAGATGGCT GAAGTAACAC GCGTGGATGC AGTTTGGCCT GGTTGGGGTC     540

ATGCATCTGA AAACCCCGAA TTACCTGATG CCCTAGATGC AAAAGGAATC ATATTTCTTG     600

GTCCTCCAGC ATCTTCAATG GCAGCACTGG GAGATAAGAT TGGTTCTTCG TTGATTGCAC     660

AAGCTGCTGA TGTACCCACT CTGCCATGGA GTGGTTCCCA TGTAAGTAAA TTTACTCTTG     720

TTAAGCTTAG CTTGTGTACC AGAGGTATAT ATTTTCATTT TTATATACTG AATTCCTATG     780

TTTTCAGGTT AAAATACCTC CTAATAGCAA CTTGGTAACC ATCCCAGAGG AGATCTACCG     840

GCAAGCATGT GTCTACACAA CTGAAGAAGC GATTGCTAGC TGTCAAGTTG TCGGTTACCC     900

AGCAATGATC AAAGCATCGT GGGGTGGTGG TGGTAAAGGA ATCAGGAAGG TCAGCTTCTG     960

TAGATATGCC TTTTGATTGT GGACTAAGCC GATTACTATA TAAGTACTTA TTCTGGTTTT    1020

AAATTTATAG GTTCATAATG ATGATGAGGT TAGGGCTCTA TTCAAGCAAG TTCAGGGTGA    1080

GGTCCCAGGC TCACCAATAT TCATAATGAA GGTTGCGTCA CAGGTATGGC TGCTTAACTA    1140

TATCTCTTGA TCGAAGCTTA GCTGAGTTCT TATCTGGTTA CTTTACTAGA GAATTTAAAG    1200

TAGTAATGCA TTGCTTTTCT TTACATTTCA TTTTTTCTAA TTTTTTTTTT GTATAGAGTC    1260

GGCATCTAGA GGTCCAGCTG CTCTGTGACA AGCATGGAAA TGTTTCAGCT CTGCATAGCC    1320

GTGATTGTAG CGTCCAGAGA AGACATCAAA AGGTTTGTTA GTGGTTGATT CTGGATTTTT    1380

AATTGTCTGG TTAGTGGTTA TATAGAAAAA CATTCTGTCC ATTTATTCTT ATATAGTTAT    1440

ATACATCAAT TTTTGTTCTC CAACTGAGTT ATAGTCCCTT TTAGCGATTG CAAATTATTG    1500

CATGAGCTCT TACTTTATCG TTTGTATCGT AGATCATAGA GGAGGGTCCA ATTACTGTGG    1560

CTCCGCCAGA AACTGTCAAG AAACTTGAAC AAGCAGCTAG AAGGTTGGCT AAGAGTGTTA    1620

ACTATGTTGG AGCTGCTACT ATTGAGTATC TCTACAGTAT GGACACTGGG GAGTACTACT    1680

TCTTAGAGCT TAACCCTCGC TTACAGGTTG GTTCATACTG CAGCTTTTTT TGCGTTGAAA    1740

TATATTGAAG GTCCGGACTT GAAAATTGAA TGACTTGTTT AACTTGATGT TTGAGGTCAG    1800
```

```
GTTGAGCATC CTGTCACTGA GTGGATTGCC GAGATAAATC TTCCTGCTGC CCAAGTTGCT    1860

GTGGGGATGG GAATTCCTCT CTGGCAAATC CCTGGTATAA TCTACGTCCT TATTTCTTAC    1920

AGGCAGCGGT TCCTCTTCTT TATCCATGCA CACGAATAAT GTACTGTCTG TTTCTCTTTA    1980

ATTTCGTAGA GATAAGACGG TTCTATGGAA TAGAACATGG TGGAGGTTAT GATTCTTGGC    2040

GAAAAACATC TGTTGTAGCC TTCCCTTTTG ACTTTGATAA AGCTCAATCT ATAAGGCCAA    2100

AAGGTCATTG TGTGGCTGTA CGTGTGACAA GTGAGGATCC TGATGACGGG TTCAAACCAA    2160

CCAGCGGTAG AGTTCAGGTA ATGTGATATC TGTGGAATGC AAAGTGAAAG TTCATTCACT    2220

GAGAACTCTG TGGGTAACAC TTGTATGAAC TTGCAACAGG AGTTGAGTTT TAAGAGCAAG    2280

CCAAATGTGT GGGCGTACTT CTCTGTCAAG GTAATTATAT CTATAGAGAC TCTGCTATAT    2340

AAGTGTTTCA CAATGTTTTA AATTTTACGA CTACTTTTTT ACAGTCTGGT GGAGGCATCC    2400

ACGAGTTCTC GGATTCCCAG TTTGGTAAGT TGAATGAAAA AAATGTATTT GGCTGCTAG    2460

GTTCTTTTCT TGAGTTTACA AAAATTGAAA CTTTCTTTAA TCTTCCATTC AGGACATGTT    2520

TTTGCATTTG GGGAATCCAG AGCCCTGGCG ATAGCGAATA TGGTTCTTGG GCTAAAAGAA    2580

ATTCAGATCC GTGGAGAAAT TAGGACTAAC GTTGACTACA CGATCGACCT TTTACATGTA    2640

CGTTTCTTCT TGCACACAAA CTTACACTCT GTGTATGCAA TACCCTGACA AGATCATTTC    2700

AATTGTCAAC CAGGCTTCTG ATTACCGTGA TAACAAAATT CACACTGGTT GGTTGGATAG    2760

TAGGATTGCT ATGCGGGTCA GAGCTGAGAG GCCTCCATGG TATCTCTCTG TTGTCGGCGG    2820

AGCTCTCTAT GTAAGAACCT CTTTCTCAGA GATTTATTTG TCTTGAAAAG TTTCTATCTG    2880

GTGACGAAAT GTTCTATCTG TCCAGAAAGC ATCAGCGACC AGTGCTGCTG TGGTTTCAGA    2940

TTACGTTGGT TATCTGGAGA AGGGGCAAAT CCCTCCAAAG GTAATCCAAT ACCAGGGATC    3000

TCTTTTGCCT TTCTAGTAAT GTTCTTGTAG CTTACTTTTT CTCTCTTAAC TTGCAGCATA    3060

TATCTCTTGT ACATTCTCAA GTGTCTCTGA ATATTGAAGG AAGTAAATAT ACGGTATTCG    3120

CCTACTATCA AAATTTTACG TCTCTGCAAT TTCGTATTTT CCTCTGCCAT ATTATTTTTG    3180

CGCTGAAGAT ATTGTTACCA GGCTTACTAA CATGAACATA ACTGTTCTAG ATTGATGTAG    3240

TCCGGGGTGG ATCAGGAACC TACAGGCTAA GAATGAACAA GTCAGAAGTG GTAGCAGAAA    3300

TACACACTCT ACGTGATGGA GGTCTGTTGA TGCAGGCAAG TTTTCTGCCT TTGTTCTATA    3360

TTACAAGACA AGGACATACA TGTGTCGCGC AGAAAAAAAC TTCTGGAGAA TCTCACTTCC    3420

TTTTCTTGTT TTCACTGTCA TTGCAGTTGG ATGGCAAAAG CCATGTGATA TATGCAGAGG    3480

AAGAAGCTGC AGGAACTCGT CTTCTCATTG ATGGAAGAAC TTGTTTGCTA CAGGTTTCTG    3540

CTAATTTTTT TGTGTGTTTA CCATTTTACT TCACGTTTCT CTGAAGTCAT CTTTAGCTTT    3600

TAAGCTGTCT GTCAATTTTG GCTTATTCAG AATGACCACG ATCCATCAAA GTTAATGGCT    3660

GAGACACCGT GCAAGTTGAT GAGGTATTTG ATTTCCGACA ACAGCAATAT TGACGCTGAT    3720

ACGCCTTATG CCGAAGTTGA GGTCATGAAG ATGTGCATGC CACTTCTTTC ACCTGCTTCA    3780

GGAGTTATCC ATTTTAAAAT GTCTGAAGGA CAAGCCATGC AGGTTCACTT CATTGCTAAA    3840

CAAAAAGCCT ACAGTTCTGT TTAAATTGAT TAACCCATCC ATTATTTTTT TCACAGGCTG    3900

GTGAACTTAT AGCCAATCTT GATCTTGATG ATCCTTCTGC TGTAAGAAAG GCCGAACCCT    3960

TCCATGGAAG TTTCCCAAGA TTAGGGCTTC CAACTGCAAT ATCCGGTAGA GTTCATCAGA    4020

GATGTGCCGC AACATTAAAT GCTGCACGCA TGATTCTTGC TGGCTATGAG CATAAAGTAG    4080

ATGAGGTAAA CACTGTTTGT TTTTCCTATT TGATCCAACT TTTCTACTAG ATTATTTGAC    4140

TATGAGATAG CTCATACGTT GCAGGTTGTT CAAGACTTAC TTAATTGCCT TGATAGCCCT    4200
```

```
GAACTCCCAT TTCTTCAGTG GCAAGAGTGC TTTGCAGTTC TGGCGACACG ACTACCTAAA      4260

AATCTCAGGA ACATGGTAAA CACCTGTGTA GTATTCATAA TCCGGTTTCT TATATATTGA      4320

TATTTGTTTT GAGTTCAAGA CTTTTAATCA TATCTAAATA AAACTCTTTA TCAGCTAGAA      4380

TCAAAGTATA GGGAATTTGA GAGTATTTCC AGAAACTCTT TGACCACCGA TTTCCCTGCC      4440

AAACTTTTAA AAGGCATTCT TGAGGTAATT GACTATTATT TCTTCCATTA GAATTACCAT      4500

CCTGTTTCTT ACTCTCTGAA TTTTTTCTGT CTACTTCTTG CAACAGGCAC ATTTATCTTC      4560

TTGTGATGAG AAAGAGAGAG GTGCCCTTGA AAGGCTCATT GAACCATTGA TGAGCCTTGC      4620

AAAATCTTAT GAAGGTGGTA GAGAAAGTCA TGCCCGTGTT ATTGTTCATT CTCTCTTTGA      4680

AGAATATCTA TCAGTAGAAG AATTATTCAA TGATAACATG CTGGTATTAT ATGGCTCAAT      4740

AGCTAATTAA CAGATTTTTG GTTACTAGCG ATGTCTGAGC GTCTAAATAA TCATTTTATT      4800

TTTCTTGAAT AGGCTGATGT TATAGAACGC ATGCGTCAGC TATACAAGAA AGATCTGTTG      4860

AAAATTGTGG ATATAGTGCT CTCACACCAG GTCTGTGATC ATCTTTCTCA GACCAGGTTT      4920

TTTCTTTCCG TCATGACTAT GTCACTGAAT TGGTTCTTCT TTTCAGGGCA TAAAAAACAA      4980

AAACAAACTC GTTCTCCGGC TCATGGAGCA GCTTGTTTAC CCTAATCCTG CTGCTTACAG      5040

AGATAAACTT ATTCGATTCT CAACACTTAA CCATACTAAC TACTCTGAGG TGCGTTTGGT      5100

TGCTTTATGT TTTATAATAT TTTTGTCTAC ACTCTCAACT AATGATCAGT TTGTGTGTGT      5160

AGTTGGCGCT CAAGGCGAGT CAATTACTTG AACAGACCAA ACTAAGTGAG CTTCGTTCAA      5220

ACATTGCTAG AAGCCTTTCA GAGTTAGAAA TGTTTACAGA GGACGGAGAA AATATGGATA      5280

CTCCCAAGAG GAAAAGTGCC ATTAATGAAA GAATAGAAGA TCTTGTAAGC GCATCTTTAG      5340

CTGTTGAAGA CGCTCTCGTG GGACTATTTG ACCATAGCGA TCACACACTT CAAAGACGGG      5400

TTGTTGAGAC TTATATTCGC AGATTATACC AGGTTCGAGT TCATTCTTCC GCACCCTTAT      5460

TGTTCAAAAT TCTTTTTGTA CTGCAATTGA TTACAGAAAA TTTTGACTTC ATTTTAACCC      5520

GACTCTTGTC ATCAGCCCTA CGTCGTTAAA GATAGCGTGA GGATGCAGTG GCACCGTTCT      5580

GGTCTTCTTG CTTCCTGGGA GTTCCTAGAG GAGCATATGG AAAGAAAAAA CATTGGCTTA      5640

GACGATCCCG ACACATCTGA AAAAGGATTG GTTGAGAAGC GTAGTAAGAG AAAATGGGGG      5700

GCTATGGTTA TAATCAAATC TTTGCAGTTT CTTCCAAGTA TAATAAGTGC AGCATTGAGA      5760

GAAACAAAGC ACAACGACTA TGAAACTGCC GGAGCTCCTT TATCTGGCAA TATGATGCAC      5820

ATTGCTATTG TGGGCATCAA CAACCAGATG AGTCTGCTTC AGGACAGGTA CTTGACACAG      5880

TATAAACTAG CTTTGGTGAT ATAGTGTCTA GCTAATCTGT TATCATTTCT GGTTTGTTTA      5940

TCTCAGTGGG GATGAAGACC AAGCTCAGGA AAGAGTAAAC AAGTTGGCCA AAATTCTTAA      6000

AGAGGAAGAA GTGAGTTCAA GCCTCTGTTC TGCCGGTGTT GGTGTAATCA GCTGTATAAT      6060

TCAGCGAGAT GAAGGACGAA CACCCATGAG ACATTCTTTC CATTGGTCGT GGAGAAACA      6120

GTATTATGTA GAAGAGCCGT TGCTGCGTCA TCTTGAACCT CCTCTGTCCA TTTACCTTGA      6180

GTTGGTATGA TCATGACCGA TGAAATTTCT TGTTTAAAGC ATATCATATT CTTTTTAATG      6240

GCTATTTACT GTTTGTCTGA TGCAGGATAA GCTGAAAGGA TACTCAAATA TACAATATAC      6300

GCCTTCTCGA GATCGTCAAT GGCATCTGTA TACTGTTACA GACAAGCCAG TGCCAATCAA      6360

GAGGATGTTC CTGAGATCTC TTGTTCGACA GGCTACAATG AACGATGGAT TTATATTGCA      6420

GCAAGGGCAG GATAAGCAGC TTAGCCAAAC ACTGATCTCC ATGGCGTTTA CGTCGAAATG      6480

TGTTCTGAGG TCTTTGATGG ATGCCATGGA GGAACTGGAA CTGAATGCCC ATAATGCTGC      6540

AATGAAACCA GATCACGCAC ATATGTTTCT TTGCATATTG CGTGACGAGC AGATAGATGA      6600
```

-continued

| | | | | | |
|---|---|---|---|---|---|
|TCTTGTGCCT|TTCCCCAGGT|TGCTATGGCT|GTGTCCTTGA|CAAGTTATTG|TTTGTAATGT|6660|
|CAGACAATAT|CCTAATAATA|TCAACGTGTT|TCTTACAGGA|GAGTTGAAGT|GAATGCGGAG|6720|
|GATGAAGAAA|CTACAGTTGA|AATGATCTTA|GAAGAAGCAG|CACGAGAGAT|ACATAGATCT|6780|
|GTTGGAGTGA|GAATGCATAG|GTTGGGCGTG|TGCGAGTGGG|AAGTGCGGCT|GTGGTTGGTG|6840|
|TCCTCTGGAC|TGGCATGTGG|TGCTTGGAGG|GTTGTGGTTG|CAAACGTGAC|AGGCCGTACA|6900|
|TGCACTGTCC|ACGTAAGTTC|CGCTTACAAA|AAATTTGGTT|GTACAAACAA|TACAGAGAGT|6960|
|AAGAGTACAC|ATCTCGATGA|CTTACCTGCT|GTGATTTAAT|ATTTCAGATA|TACCGAGAAG|7020|
|TTGAAACTCC|TGGAAGAAAC|AGTTTAATCT|ACCACTCAAT|AACCAAGAAG|GGACCTTTGC|7080|
|ATGAAACACC|AATCAGTGAT|CAATATAAGC|CCCTGGGATA|TCTCGACAGG|CAACGTTTAG|7140|
|CAGCAAGGAG|GAGTAACACT|ACTTATTGCT|ATGACTTCCC|GTTGGTTTGT|TACTGAATTC|7200|
|ATAAGATTCA|CACATACGCT|TACTCTTTTG|GCTATTTCCA|ACCCCCCTTA|TGTTATTTCT|7260|
|TTCCTTTTCA|GGCATTTGGG|ACAGCCTTGG|AACTGTTGTG|GGCATCACAA|CACCCAGGAG|7320|
|TTAAGAAACC|ATATAAGGAT|ACTCTGATCA|ATGTTAAAGA|GCTTGTATTC|TCAAAACCAG|7380|
|AAGGTTCTTC|GGGTACATCT|CTAGATCTGG|TTGAAAGACC|ACCCGGTCTC|AACGACTTTG|7440|
|GGATGGTTGC|CTGGTGCCTA|GATATGTCGA|CCCCAGAGTT|TCCTATGGGG|CGGAAACTTC|7500|
|TCGTGATTGC|GAATGATGTC|ACCTTCAAAG|CTGGTTCTTT|TGGTCCTAGA|GAGGACGCGT|7560|
|TTTTCCTTGC|TGTTACTGAA|CTCGCTTGTG|CCAAGAAGCT|TCCCTTGATT|TACTTGGCAG|7620|
|CAAATTCTGG|TGCCCGACTT|GGGGTTGCTG|AAGAAGTCAA|AGCCTGCTTC|AAAGTTGGAT|7680|
|GGTCGGATGA|AATTTCCCCT|GAGAATGGTT|TTCAGTATAT|ATACCTAAGC|CCTGAAGACC|7740|
|ACGAAAGGAT|TGGATCATCT|GTCATTGCCC|ATGAAGTAAA|GCTCTCTAGT|GGGGAAACTA|7800|
|GGTGGGTGAT|TGATACGATC|GTTGGCAAAG|AAGATGGTAT|TGGTGTAGAG|AACTTAACAG|7860|
|GAAGTGGGGC|CATAGCGGGT|GCTTACTCAA|AGGCATACAA|TGAAACTTTT|ACTTTAACCT|7920|
|TTGTTAGTGG|AAGAACGGTT|GGAATTGGTG|CTTATCTTGC|CCGCCTAGGT|ATGCGGTGCA|7980|
|TACAGAGACT|TGATCAGCCG|ATCATCTTGA|CTGGCTTCTC|TACACTCAAC|AAGTTACTTG|8040|
|GGCGTGAGGT|CTATAGCTCT|CACATGCAAC|TGGGTGGCCC|GAAAATCATG|GCACAAATG|8100|
|GTGTTGTTCA|TCTTACAGTC|TCAGATGATC|TTGAAGGCGT|ATCAGCAATT|CTCAACTGGC|8160|
|TCAGCTACAT|TCCTGCTTAC|GTGGGTGGTC|CTCTTCCTGT|TCTTGCCCCT|TTAGATCCAC|8220|
|CGGAGAGAAT|TGTGGAGTAT|GTCCCAGAGA|ACTCTTGCGA|CCCACGAGCG|GCTATAGCTG|8280|
|GGGTCAAAGA|CAATACCGGT|AAATGGCTTG|GAGGTATCTT|TGATAAAAAT|AGTTTCATTG|8340|
|AGACTCTTGA|AGGCTGGGCA|AGGACGGTAG|TGACTGGTAG|AGCCAAGCTC|GGGGAATAC|8400|
|CCGTTGGAGT|TGTTGCAGTT|GAGACACAGA|CTGTCATGCA|GATCATCCCA|GCCGATCCTG|8460|
|GACAGCTTGA|CTCTCATGAA|AGAGTGGTTC|CGCAAGCAGG|GCAAGTCTGG|TTTCCTGATT|8520|
|CAGCGGCCAA|GACTGCTCAA|GCGCTTATGG|ATTTCAACCG|GGAAGAGCTT|CCATTGTTTA|8580|
|TCCTAGCGAA|CTGGAGAGGG|TTTTCAGGTG|GGCAGAGAGA|TCTTTTCGAA|GGAATACTTC|8640|
|AGGCAGGTTC|AACTATAGTA|GAAAATCTGA|GAACCTATCG|TCAGCCAGTG|TTTGTGTACA|8700|
|TCCCAATGAT|GGGAGAGCTG|CGCGGTGGAG|CGTGGGTTGT|TGTTGACAGC|CAGATAAATT|8760|
|CGGATTATGT|TGAAATGTAT|GCTGATGAAA|CAGCTCGTGG|AAATGTGCTT|GAGCCAGAAG|8820|
|GGACAATAGA|GATAAAATTT|AGAACAAAAG|AGCTATTAGA|GTGCATGGGA|AGGTTGGACC|8880|
|AGAAGCTAAT|CAGTCTGAAA|GCAAAACTGC|AAGATGCCAA|GCAAAGCGAG|GCCTATGCAA|8940|
|ACATCGAGCT|TCTCCAGCAA|CAGATTAAAG|CCCGAGAGAA|ACAGCTTTTA|CCAGTTTATA|9000|

```
TCCAAATCGC CACCAAATTT GCAGAACTTC ATGACACTTC CATGAGAATG GCTGCAAAGG    9060

GAGTGATCAA AAGTGTTGTG GAATGGAGCG GCTCGCGGTC CTTCTTCTAC AAAAAGCTCA    9120

ATAGGAGAAT CGCTGAGAGC TCTCTTGTGA AAAACGTAAG AGAAGCATCT GGAGACAACT    9180

TAGCATATAA ATCTTCAATG CGTCTGATTC AGGATTGGTT CTGCAACTCT GATATTGCAA    9240

AGGGGAAAGA AGAAGCTTGG ACAGACGACC AAGTGTTCTT TACATGGAAG ACAATGTTA     9300

GTAACTACGA GTTGAAGCTG AGCGAGTTGA GAGCGCAGAA ACTACTGAAC CAACTTGCAG    9360

AGATTGGGAA TTCCTCAGAT TTGCAAGCTC TGCCACAAGG ACTTGCTAAT CTTCTAAACA    9420

AGGTATAAAA CGAAACCCTC CAGAAAAACA GAGGTTTTGG TCCTCTAGTA TTCTTATCTG    9480

TATGGCTCGG TTTTTAAAGG CCTAAGTAAA TATTTGTGAT GCAGGTGGAG CCGTCGAAAA    9540

GAGAAGAGCT GGTGGCTGCT ATTCGAAAGG TCTTGGGTTG A                        9581

(2) INFORMATION FOR SEQ ID NO:2:

(i) SEQUENCE CHARACTERISTICS:
        (A) LENGTH: 6765 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

ATGGCTGGCT CGGTTAACGG GAATCATAGT GCTGTAGGAC CTGGTATAAA TTATGAGACG      60

GTGTCTCAAG TGGATGAGTT CTGTAAAGCA CTTAGAGGGA AAAGGCCGAT CCATAGTATT     120

TTGATAGCTA ACAATGGAAT GGCGGCTGTG AAGTTTATAC GTAGTGTCAG AACATGGGCT     180

TATGAAACAT TTGGTACGGA AAAAGCCATA TTGTTGGTGG GGATGGCAAC CCCTGAAGAC     240

ATGCGGATCA ATGCGGAGAC TATCAGAATC GCTGATCAGT TTGTTGAGGT TCCCGGAGGA     300

ACCAACAATA ACAATTATGC TAACGTTCAG CTGATTGTGG AGATGGCTGA AGTAACACGC     360

GTGGATGCAG TTTGGCCTGG TTGGGGTCAT GCATCTGAAA ACCCCGAATT ACCTGATGCC     420

CTAGATGCAA AAGGAATCAT ATTTCTTGGT CCTCCAGCAT CTTCAATGGC AGCACTGGGA     480

GATAAGATTG GTTCTTCGTT GATTGCACAA GCTGCTGATG TACCCACTCT GCCATGGAGT     540

GGTTCCCATG TTAAAATACC TCCTAATAGC AACTTGGTAA CCATCCCAGA GGAGATCTAC     600

CGGCAAGCAT GTGTCTACAC AACTGAAGAA GCGATTGCTA GCTGTCAAGT TGTCGGTTAC     660

CCAGCAATGA TCAAAGCATC GTGGGGTGGT GGTGGTAAAG GAATCAGGAA GGTTCATAAT     720

GATGATGAGG TTAGGGCTCT ATTCAAGCAA GTTCAGGGTG AGGTCCCAGG CTCACCAATA     780

TTCATAATGA AGGTTGCGTC ACAGAGTCGG CATCTAGAGG TCCAGCTGCT CTGTGACAAG     840

CATGGAAATG TTTCAGCTCT GCATAGCCGT GATTGTAGCG TCCAGAGAAG ACATCAAAAG     900

ATCATAGAGG AGGGTCCAAT TACTGTGGCT CCGCCAGAAA CTGTCAAGAA ACTTGAACAA     960

GCAGCTAGAA GGTTGGCTAA GAGTGTTAAC TATGTTGGAG CTGCTACTGT TGAGTATCTC     1020

TACAGTATGG ACACTGGGGA GTACTACTTC TTAGAGCTTA ACCCTCGCTT ACAGGTTGAG     1080

CATCCTGTCA CTGAGTGGAT TGCCGAGATA ATCTTCCTG CTGCCCAAGT TGCTGTGGGG     1140

ATGGGAATTC CTCTCTGGCA AATCCCTGAG ATAAGACGGT TCTATGGAAT AGAACATGGT     1200

GGAGGTTATG ATTCTTGGCG AAAAACATCT GTTGTAGCCT TCCCTTTTGA CTTTGATAAA     1260

GCTCAATCTA TAAGGCCAAA AGGTCATTGT GTGGCTGTAC GTGTGACAAG TGAGGATCCT     1320

GATGACGGGT TCAAACCAAC CAGCGGTAGA GTTCAGGAGT TGAGTTTTAA GAGCAAGCCA     1380

AATGTGTGGG CGTACTTCTC TGTCAAGTCT GGTGGAGGCA TCCACGAGTT CTCGGATTCC     1440
```

```
CAGTTTGGAC ATGTTTTTGC ATTTGGGGAA TCCAGAGCCC TGGCGATAGC GAATATGGTT    1500

CTTGGGCTAA AAGAAATTCA GATCCGTGGA GAAATTAGGA CTAACGTTGA CTACACGATC    1560

GACCTTTTAC ATGCTTCTGA TTACCGTGAT AACAAAATTC ACACTGGTTG GTTGGATAGT    1620

AGGATTGCTA TGCGGGTCAG AGCTGAGAGG CCTCCATGGT ATCTCTCTGT TGTCGGCGGA    1680

GCTCTCTATA AAGCATCAGC GACCAGTGCT GCTGTGGTTT CAGATTACGT TGGTTATCTG    1740

GAGAAGGGGC AAATCCCTCC AAAGCATATA TCTCTTGTAC ATTCTCAAGT GTCTCTGAAT    1800

ATTGAAGGAA GTAAATATAC GATTGATGTA GTCCGGGGTG GATCAGGAAC CTACAGGCTA    1860

AGAATGAACA AGTCAGAAGT GGTAGCAGAA ATACACACTC TACGTGATGG AGGTCTGTTG    1920

ATGCAGTTGG ATGGCAAAAG CCATGTGATA TATGCAGAGG AAGAAGCTGC AGGAACTCGT    1980

CTTCTCATTG ATGGAAGAAC TTGTTTGCTA CAGAATGACC ACGATCCATC AAAGTTAATG    2040

GCTGAGACAC CGTGCAAGTT GATGAGGTAT TTGATTTCCG ACAACAGCAA TATTGACGCT    2100

GATACGCCTT ATGCCGAAGT TGAGGTCATG AAGATGTGCA TGCCACTTCT TTCACCTGCT    2160

TCAGGAGTTA TCCATTTTAA AATGTCTGAA GGACAAGCCA TGCAGGCTGG TGAACTTATA    2220

GCCAATCTTG ATCTTGATGA TCCTTCTGCT GTAAGAAAGG CCGAACCCTT CCATGGAAGT    2280

TTCCCAAGAT TAGGGCTTCC AACTGCAATA TCCGGTAGAG TTCATCAGAG ATGTGCCGCA    2340

ACATTAAATG CTGCACGCAT GATTCTTGCT GGCTATGAGC ATAAAGTAGA TGAGGTTGTT    2400

CAAGACTTAC TTAATTGCCT TGATAGCCCT GAACTCCCAT TCTTCAGTG GCAAGAGTGC    2460

TTTGCAGTTC TGGCGACACG ACTACCTAAA AATCTCAGGA ACATGCTAGA ATCAAAGTAT    2520

AGGGAATTTG AGAGTATTTC CAGAAACTCT TTGACCACCG ATTTCCCTGC CAAACTTTTA    2580

AAAGGCATTC TTGAGGCACA TTTATCTTCT TGTGATGAGA AAGAGAGAGG TGCCCTTGAA    2640

AGGCTCATTG AACCATTGAT GAGCCTTGCA AAATCTTATG AAGGTGGTAG AGAAAGTCAT    2700

GCCCGTGTTA TTGTTCATTC TCTCTTTGAA GAATATCTAT CAGTAGAAGA ATTATTCAAT    2760

GATAACATGC TGGCTGATGT TATAGAACGC ATGCGTCAGC TATACAAGAA AGATCTGTTG    2820

AAAATTGTGG ATATAGTGCT CTCACACCAG GGCATAAAAA ACAAAAACAA ACTCGTTCTC    2880

CGGCTCATGG AGCAGCTTGT TTACCCTAAT CCTGCTGCTT ACAGAGATAA ACTTATTCGA    2940

TTCTCAACAC TTAACCATAC TAACTACTCT GAGTTGGCGC TCAAGGCGAG TCAATTACTT    3000

GAACAGACCA AACTAAGTGA GCTTCGTTCA AACATTGCTA GAAGCCTTTC AGAGTTAGAA    3060

ATGTTTACAG AGGACGGAGA AAATATGGAT ACTCCCAAGA GGAAAAGTGC CATTAATGAA    3120

AGAATAGAAG ATCTTGTAAG CGCATCTTTA GCTGTTGAAG ACGCTCTCGT GGGACTATTT    3180

GACCATAGCG ATCACACACT TCAAAGACGG GTTGTTGAGA CTTATATTCG CAGATTATAC    3240

CAGCCCTACG TCGTTAAAGA TAGCGTGAGG ATGCAGTGGC ACCGTTCTGG TCTTCTTGCT    3300

TCCTGGGAGT TCCTAGAGGA GCATATGGAA AGAAAAAACA TTGGCTTAGA CGATCCCGAC    3360

ACATCTGAAA AAGGATTGGT TGAGAAGCGT AGTAAGAGAA AATGGGGGC TATGGTTATA    3420

ATCAAATCTT TGCAGTTTCT TCCAAGTATA ATAAGTGCAG CATTGAGAGA AACAAAGCAC    3480

AACGACTATG AAACTGCCGG AGCTCCTTTA TCTGGCAATA TGATGCACAT TGCTATTGTG    3540

GGCATCAACA ACCAGATGAG TCTGCTTCAG GACAGTGGGG ATGAAGACCA AGCTCAGGAA    3600

AGAGTAAACA AGTTGGCCAA AATTCTTAAA GAGGAAGAAG TGAGTTCAAG CCTCTGTTCT    3660

GCCGGTGTTG GTGTAATCAG CTGTATAATT CAGCGAGATG AAGGACGAAC ACCCATGAGA    3720

CATTCTTTCC ATTGGTCGTT GGAGAAACAG TATTATGTAG AAGAGCCGTT GCTGCGTCAT    3780

CTTGAACCTC CTCTGTCCAT TTACCTTGAG TTGGATAAGC TGAAAGGATA CTCAAATATA    3840
```

```
CAATATACGC CTTCTCGAGA TCGTCAATGG CATCTGTATA CTGTTACAGA CAAGCCAGTG   3900

CCAATCAAGA GGATGTTCCT GAGATCTCTT GTTCGACAGG CTACAATGAA CGATGGATTT   3960

ATATTGCAGC AAGGGCAGGA TAAGCAGCTT AGCCAAACAC TGATCTCCAT GGCGTTTACG   4020

TCGAAATGTG TTCTGAGGTC TTTGATGGAT GCCATGGAGG AACTGGAACT GAATGCCCAT   4080

AATGCTGCAA TGAAACCAGA TCACGCACAT ATGTTTCTTT GCATATTGCG TGACGAGCAG   4140

ATAGATGATC TTGTGCCTTT CCCCAGGAGA GTTGAAGTGA ATGCGGAGGA TGAAGAAACT   4200

ACAGTTGAAA TGATCTTAGA AGAAGCAGCA CGAGAGATAC ATAGATCGT TGGAGTGAGA    4260

ATGCATAGGT TGGGCGTGTG CGAGTGGGAA GTGCGGCTGT GGTTGGTGTC CTCTGGACTG   4320

GCATGTGGTG CTTGGAGGGT TGTGGTTGCA AACGTGACAG GCCGTACATG CACTGTCCAC   4380

ATATACCGAG AAGTTGAAAC TCCTGGAAGA AACAGTTTAA TCTACCACTC AATAACCAAG   4440

AAGGGACCTT TGCATGAAAC ACCAATCAGT GATCAATATA AGCCCCTGGG ATATCTCGAC   4500

AGGCAACGTT TAGCAGCAAG GAGGAGTAAC ACTACTTATT GCTATGACTT CCCGTTGGCA   4560

TTTGGGACAG CCTTGGAACT GTTGTGGGCA TCACAACACC CAGGAGTTAA GAAACCATAT   4620

AAGGATACTC TGATCAATGT TAAAGAGCTT GTATTCTCAA AACCAGAAGG TTCTTCGGGT   4680

ACATCTCTAG ATCGGTTGA AAGACCACCC GGTCTCAACG ACTTTGGGAT GGTTGCCTGG    4740

TGCCTAGATA TGTCGACCCC AGAGTTTCCT ATGGGGCGGA AACTTCTCGT GATTGCGAAT   4800

GATGTCACCT TCAAAGCTGG TTCTTTTGGT CCTAGAGAGG ACGCGTTTTT CCTTGCTGTT   4860

ACTGAACTCG CTTGTGCCAA GAAGCTTCCC TTGATTTACT GGCAGCAAA  TTCTGGTGCC   4920

CGACTTGGGG TTGCTGAAGA AGTCAAAGCC TGCTTCAAAG TTGGATGGTC GGATGAAATT   4980

TCCCCTGAGA ATGGTTTTCA GTATATATAC CTAAGCCCTG AAGACCACGA AAGGATTGGA   5040

TCATCTGTCA TTGCCCATGA AGTAAAGCTC TCTAGTGGGG AAACTAGGTG GGTGATTGAT   5100

ACGATCGTTG GCAAAGAAGA TGGTATTGGT GTAGAGAACT TAACAGGAAG TGGGGCCATA   5160

GCGGGTGCTT ACTCAAAGGC ATACAATGAA ACTTTTACTT TAACCTTTGT TAGTGGAAGA   5220

ACGGTTGGAA TTGGTGCTTA TCTTGCCCGC CTAGGTATGC GGTGCATACA GAGACTTGAT   5280

CAGCCGATCA TCTTGACTGG CTTCTCTACA CTCAACAAGT TACTTGGGCG TGAGGTCTAT   5340

AGCTCTCACA TGCAACTGGG TGGCCCGAAA ATCATGGGCA CAAATGGTGT TGTTCATCTT   5400

ACAGTCTCAG ATGATCTTGA AGGCGTATCA GCAATTCTCA ACTGGCTCAG CTACATTCCT   5460

GCTTACGTGG GTGGTCCTCT TCCTGTTCTT GCCCCTTTAG ATCCACCGGA GAGAATTGTG   5520

GAGTATGTCC CAGAGAACTC TTGCGACCCA CGAGCGGCTA TAGCTGGGGT CAAAGACAAT   5580

ACCGGTAAAT GGCTTGGAGG TATCTTTGAT AAAAATAGTT TCATTGAGAC TCTTGAAGGC   5640

TGGGCAAGGA CGGTAGTGAC TGGTAGAGCC AAGCTCGGGG GAATACCCGT TGGAGTTGTT   5700

GCAGTTGAGA CACAGACTGT CATGCAGATC ATCCCAGCCG ATCCTGGACA GCTTGACTCT   5760

CATGAAAGAG TGGTTCCGCA AGCAGGGCAA GTCTGGTTTC CTGATTCAGC GGCCAAGACT   5820

GCTCAAGCGC TTATGGATTT CAACCGGAA  GAGCTTCCAT TGTTTATCCT AGCGAACTGG   5880

AGAGGGTTTT CAGGTGGGCA GAGAGATCTT TTCGAAGGAA TACTTCAGGC AGGTTCAACT   5940

ATAGTAGAAA ATCTGAGAAC CTATCGTCAG CCAGTGTTTG TGTACATCCC AATGATGGGA   6000

GAGCTGCGCG GTGGAGCGTG GGTTGTTGTT GACAGCCAGA TAAATTCGGA TTATGTTGAA   6060

ATGTATGCTG ATGAAACAGC TCGTGGAAAT GTGCTTGAGC CAGAAGGGAC AATAGAGATA   6120

AAATTTAGAA CAAAAGAGCT ATTAGAGTGC ATGGGAAGGT TGGACCAGAA GCTAATCAGT   6180

CTGAAAGCAA AACTGCAAGA TGCCAAGCAA AGCGAGGCCT ATGCAAACAT CGAGCTTCTC   6240
```

```
CAGCAACAGA TTAAAGCCCG AGAGAAACAG CTTTTACCAG TTTATATCCA AATCGCCACC    6300

AAATTTGCAG AACTTCATGA CACTTCCATG AGAATGGCTG CAAAGGGAGT GATCAAAAGT    6360

GTTGTGGAAT GGAGCGGCTC GCGGTCCTTC TTCTACAAAA AGCTCAATAG AGAATCGCT     6420

GAGAGCTCTC TTGTGAAAAA CGTAAGAGAA GCATCTGGAG ACAACTTAGC ATATAAATCT    6480

TCAATGCGTC TGATTCAGGA TTGGTTCTGC AACTCTGATA TTGCAAAGGG GAAAGAAGAA    6540

GCTTGGACAG ACGACCAAGT GTTCTTTACA TGGAAGGACA ATGTTAGTAA CTACGAGTTG    6600

AAGCTGAGCG AGTTGAGAGC GCAGAAACTA CTGAACCAAC TTGCAGAGAT TGGGAATTCC    6660

TCAGATTTGC AAGCTCTGCC ACAAGGACTT GCTAATCTTC TAAACAAGGT GGAGCCGTCG    6720

AAAAGAGAAG AGCTGGTGGC TGCTATTCGA AAGGTCTTGG GTTGA                    6765
```

(2) INFORMATION FOR SEQ ID NO:3:

(i) SEQUENCE CHARACTERISTICS:
        (A) LENGTH: 2254 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

```
Met Ala Gly Ser Val Asn Gly Asn His Ser Ala Val Gly Pro Gly Ile
1               5                   10                  15

Asn Tyr Glu Thr Val Ser Gln Val Asp Glu Phe Cys Lys Ala Leu Arg
            20                  25                  30

Gly Lys Arg Pro Ile His Ser Ile Leu Ile Ala Asn Asn Gly Met Ala
        35                  40                  45

Ala Val Lys Phe Ile Arg Ser Val Arg Thr Trp Ala Tyr Glu Thr Phe
    50                  55                  60

Gly Thr Glu Lys Ala Ile Leu Leu Val Gly Met Ala Thr Pro Glu Asp
65                  70                  75                  80

Met Arg Ile Asn Ala Glu His Ile Arg Ile Ala Asp Gln Phe Val Glu
                85                  90                  95

Val Pro Gly Gly Thr Asn Asn Asn Tyr Ala Asn Val Gln Leu Ile
            100                 105                 110

Val Glu Met Ala Glu Val Thr Arg Val Asp Ala Val Trp Pro Gly Trp
        115                 120                 125

Gly His Ala Ser Glu Asn Pro Glu Leu Pro Asp Ala Leu Asp Ala Lys
    130                 135                 140

Gly Ile Ile Phe Leu Gly Pro Pro Ala Ser Ser Met Ala Ala Leu Gly
145                 150                 155                 160

Asp Lys Ile Gly Ser Ser Leu Ile Ala Gln Ala Ala Asp Val Pro Thr
                165                 170                 175

Leu Pro Trp Ser Gly Ser His Val Lys Ile Pro Pro Asn Ser Asn Leu
            180                 185                 190

Val Thr Ile Pro Glu Glu Ile Tyr Arg Gln Ala Cys Val Tyr Thr Thr
        195                 200                 205

Glu Glu Ala Ile Ala Ser Cys Gln Val Val Gly Tyr Pro Ala Met Ile
    210                 215                 220

Lys Ala Ser Trp Gly Gly Gly Lys Gly Ile Arg Lys Val His Asn
225                 230                 235                 240

Asp Asp Glu Val Arg Ala Leu Phe Lys Gln Val Gln Gly Glu Val Pro
                245                 250                 255
```

-continued

```
Gly Ser Pro Ile Phe Ile Met Lys Val Ala Ser Gln Ser Arg His Leu
            260                 265                 270

Glu Val Gln Leu Leu Cys Asp Lys His Gly Asn Val Ser Ala Leu His
            275                 280                 285

Ser Arg Asp Cys Ser Val Gln Arg Arg His Gln Lys Ile Ile Glu Glu
290                 295                 300

Gly Pro Ile Thr Val Ala Pro Pro Glu Thr Val Lys Lys Leu Glu Gln
305                 310                 315                 320

Ala Ala Arg Arg Leu Ala Lys Ser Val Asn Tyr Val Gly Ala Ala Thr
                325                 330                 335

Ile Glu Tyr Leu Tyr Ser Met Asp Thr Gly Glu Tyr Tyr Phe Leu Glu
                340                 345                 350

Leu Asn Pro Arg Leu Gln Val Glu His Pro Val Thr Glu Trp Ile Ala
                355                 360                 365

Glu Ile Asn Leu Pro Ala Ala Gln Val Ala Val Gly Met Gly Ile Pro
370                 375                 380

Leu Trp Gln Ile Pro Glu Ile Arg Arg Phe Tyr Gly Ile Glu His Gly
385                 390                 395                 400

Gly Gly Tyr Asp Ser Trp Arg Lys Thr Ser Val Val Ala Phe Pro Phe
                405                 410                 415

Asp Phe Asp Lys Ala Gln Ser Ile Arg Pro Lys Gly His Cys Val Ala
                420                 425                 430

Val Arg Val Thr Ser Glu Asp Pro Asp Asp Gly Phe Lys Pro Thr Ser
            435                 440                 445

Gly Arg Val Gln Glu Leu Ser Phe Lys Ser Lys Pro Asn Val Trp Ala
450                 455                 460

Tyr Phe Ser Val Lys Ser Gly Gly Ile His Glu Phe Ser Asp Ser
465                 470                 475                 480

Gln Phe Gly His Val Phe Ala Phe Gly Glu Ser Arg Ala Leu Ala Ile
                485                 490                 495

Ala Asn Met Val Leu Gly Leu Lys Glu Ile Gln Ile Arg Gly Glu Ile
            500                 505                 510

Arg Thr Asn Val Asp Tyr Thr Ile Asp Leu Leu His Ala Ser Asp Tyr
            515                 520                 525

Arg Asp Asn Lys Ile His Thr Gly Trp Leu Asp Ser Arg Ile Ala Met
530                 535                 540

Arg Val Arg Ala Glu Arg Pro Pro Trp Tyr Leu Ser Val Val Gly Gly
545                 550                 555                 560

Ala Leu Tyr Lys Ala Ser Ala Thr Ser Ala Ala Val Val Ser Asp Tyr
                565                 570                 575

Val Gly Tyr Leu Glu Lys Gly Gln Ile Pro Pro Lys His Ile Ser Leu
                580                 585                 590

Val His Ser Gln Val Ser Leu Asn Ile Glu Gly Ser Lys Tyr Thr Ile
            595                 600                 605

Asp Val Val Arg Gly Gly Ser Gly Thr Tyr Arg Leu Arg Met Asn Lys
            610                 615                 620

Ser Glu Val Val Ala Glu Ile His Thr Leu Arg Asp Gly Gly Leu Leu
625                 630                 635                 640

Met Gln Leu Asp Gly Lys Ser His Val Ile Tyr Ala Glu Glu Glu Ala
                645                 650                 655

Ala Gly Thr Arg Leu Leu Ile Asp Gly Arg Thr Cys Leu Leu Gln Asn
                660                 665                 670

Asp His Asp Pro Ser Lys Leu Met Ala Glu Thr Pro Cys Lys Leu Met
            675                 680                 685
```

-continued

```
Arg Tyr Leu Ile Ser Asp Asn Ser Asn Ile Asp Ala Asp Thr Pro Tyr
    690                 695                 700

Ala Glu Val Glu Val Met Lys Met Cys Met Pro Leu Leu Ser Pro Ala
705                 710                 715                 720

Ser Gly Val Ile His Phe Lys Met Ser Glu Gly Gln Ala Met Gln Ala
                725                 730                 735

Gly Glu Leu Ile Ala Asn Leu Asp Leu Asp Asp Pro Ser Ala Val Arg
            740                 745                 750

Lys Ala Glu Pro Phe His Gly Ser Phe Pro Arg Leu Gly Leu Pro Thr
        755                 760                 765

Ala Ile Ser Gly Arg Val His Gln Arg Cys Ala Ala Thr Leu Asn Ala
    770                 775                 780

Ala Arg Met Ile Leu Ala Gly Tyr Glu His Lys Val Asp Glu Val Val
785                 790                 795                 800

Gln Asp Leu Leu Asn Cys Leu Asp Ser Pro Glu Leu Pro Phe Leu Gln
                805                 810                 815

Trp Gln Glu Cys Phe Ala Val Leu Ala Thr Arg Leu Pro Lys Asn Leu
            820                 825                 830

Arg Asn Met Leu Glu Ser Lys Tyr Arg Glu Phe Glu Ser Ile Ser Arg
        835                 840                 845

Asn Ser Leu Thr Thr Asp Phe Pro Ala Lys Leu Leu Lys Gly Ile Leu
    850                 855                 860

Glu Ala His Leu Ser Ser Cys Asp Glu Lys Glu Arg Gly Ala Leu Glu
865                 870                 875                 880

Arg Leu Ile Glu Pro Leu Met Ser Leu Ala Lys Ser Tyr Glu Gly Gly
                885                 890                 895

Arg Glu Ser His Ala Arg Val Ile Val His Ser Leu Phe Glu Glu Tyr
            900                 905                 910

Leu Ser Val Glu Glu Leu Phe Asn Asp Asn Met Leu Ala Asp Val Ile
        915                 920                 925

Glu Arg Met Arg Gln Leu Tyr Lys Lys Asp Leu Leu Lys Ile Val Asp
    930                 935                 940

Ile Val Leu Ser His Gln Gly Ile Lys Asn Lys Asn Lys Leu Val Leu
945                 950                 955                 960

Arg Leu Met Glu Gln Leu Val Tyr Pro Asn Pro Ala Ala Tyr Arg Asp
                965                 970                 975

Lys Leu Ile Arg Phe Ser Thr Leu Asn His Thr Asn Tyr Ser Glu Leu
            980                 985                 990

Ala Leu Lys Ala Ser Gln Leu Leu Glu Gln Thr Lys Leu Ser Glu Leu
        995                 1000                1005

Arg Ser Asn Ile Ala Arg Ser Leu Ser Glu Leu Glu Met Phe Thr Glu
    1010                1015                1020

Asp Gly Glu Asn Met Asp Thr Pro Lys Arg Lys Ser Ala Ile Asn Glu
1025                1030                1035                1040

Arg Ile Glu Asp Leu Val Ser Ala Ser Leu Ala Val Glu Asp Ala Leu
                1045                1050                1055

Val Gly Leu Phe Asp His Ser Asp His Thr Leu Gln Arg Arg Val Val
            1060                1065                1070

Glu Thr Tyr Ile Arg Arg Leu Tyr Gln Pro Tyr Val Val Lys Asp Ser
        1075                1080                1085

Val Arg Met Gln Trp His Arg Ser Gly Leu Leu Ala Ser Trp Glu Phe
    1090                1095                1100

Leu Glu Glu His Met Glu Arg Lys Asn Ile Gly Leu Asp Asp Pro Asp
```

```
       1105                1110                1115                1120
  Thr Ser Glu Lys Gly Leu Val Glu Lys Arg Ser Lys Arg Lys Trp Gly
                     1125                1130                1135
  Ala Met Val Ile Ile Lys Ser Leu Gln Phe Leu Pro Ser Ile Ile Ser
                     1140                1145                1150
  Ala Ala Leu Arg Glu Thr Lys His Asn Asp Tyr Glu Thr Ala Gly Ala
                     1155                1160                1165
  Pro Leu Ser Gly Asn Met Met His Ile Ala Ile Val Gly Ile Asn Asn
                     1170                1175                1180
  Gln Met Ser Leu Leu Gln Asp Ser Gly Asp Gln Ala Gln Glu
  1185                1190                1195                1200
  Arg Val Asn Lys Leu Ala Lys Ile Leu Lys Glu Glu Val Ser Ser
                     1205                1210                1215
  Ser Leu Cys Ser Ala Gly Val Gly Val Ile Ser Cys Ile Ile Gln Arg
                     1220                1225                1230
  Asp Glu Gly Arg Thr Pro Met Arg His Ser Phe His Trp Ser Leu Glu
                     1235                1240                1245
  Lys Gln Tyr Tyr Val Glu Glu Pro Leu Leu Arg His Leu Glu Pro Pro
                     1250                1255                1260
  Leu Ser Ile Tyr Leu Glu Leu Asp Lys Leu Lys Gly Tyr Ser Asn Ile
  1265                1270                1275                1280
  Gln Tyr Thr Pro Ser Arg Asp Arg Gln Trp His Leu Tyr Thr Val Thr
                     1285                1290                1295
  Asp Lys Pro Val Pro Ile Lys Arg Met Phe Leu Arg Ser Leu Val Arg
                     1300                1305                1310
  Gln Ala Thr Met Asn Asp Gly Phe Ile Leu Gln Gln Gly Gln Asp Lys
                     1315                1320                1325
  Gln Leu Ser Gln Thr Leu Ile Ser Met Ala Phe Thr Ser Lys Cys Val
                     1330                1335                1340
  Leu Arg Ser Leu Met Asp Ala Met Glu Glu Leu Glu Leu Asn Ala His
  1345                1350                1355                1360
  Asn Ala Ala Met Lys Pro Asp His Ala His Met Phe Leu Cys Ile Leu
                     1365                1370                1375
  Arg Asp Glu Gln Ile Asp Asp Leu Val Pro Phe Pro Arg Arg Val Glu
                     1380                1385                1390
  Val Asn Ala Glu Asp Glu Glu Thr Thr Val Glu Met Ile Leu Glu Glu
                     1395                1400                1405
  Ala Ala Arg Glu Ile His Arg Ser Val Gly Val Arg Met His Arg Leu
                     1410                1415                1420
  Gly Val Cys Glu Trp Glu Val Arg Leu Trp Leu Val Ser Ser Gly Leu
  1425                1430                1435                1440
  Ala Cys Gly Ala Trp Arg Val Val Ala Asn Val Thr Gly Arg Thr
                     1445                1450                1455
  Cys Thr Val His Ile Tyr Arg Glu Val Glu Thr Pro Gly Arg Asn Ser
                     1460                1465                1470
  Leu Ile Tyr His Ser Ile Thr Lys Lys Gly Pro Leu His Glu Thr Pro
                     1475                1480                1485
  Ile Ser Asp Gln Tyr Lys Pro Leu Gly Tyr Leu Asp Arg Gln Arg Leu
                     1490                1495                1500
  Ala Ala Arg Arg Ser Asn Thr Thr Tyr Cys Tyr Asp Phe Pro Leu Ala
  1505                1510                1515                1520
  Phe Gly Thr Ala Leu Glu Leu Leu Trp Ala Ser Gln His Pro Gly Val
                     1525                1530                1535
```

-continued

```
Lys Lys Pro Tyr Lys Asp Thr Leu Ile Asn Val Lys Glu Leu Val Phe
            1540                1545                1550

Ser Lys Pro Glu Gly Ser Ser Gly Thr Ser Leu Asp Leu Val Glu Arg
            1555                1560                1565

Pro Pro Gly Leu Asn Asp Phe Gly Met Val Ala Trp Cys Leu Asp Met
1570                1575                1580

Ser Thr Pro Glu Phe Pro Met Gly Arg Lys Leu Leu Val Ile Ala Asn
1585                1590                1595                1600

Asp Val Thr Phe Lys Ala Gly Ser Phe Gly Pro Arg Glu Asp Ala Phe
            1605                1610                1615

Phe Leu Ala Val Thr Glu Leu Ala Cys Ala Lys Lys Leu Pro Leu Ile
            1620                1625                1630

Tyr Leu Ala Ala Asn Ser Gly Ala Arg Leu Gly Val Ala Glu Glu Val
            1635                1640                1645

Lys Ala Cys Phe Lys Val Gly Trp Ser Asp Glu Ile Ser Pro Glu Asn
            1650                1655                1660

Gly Phe Gln Tyr Ile Tyr Leu Ser Pro Glu Asp His Glu Arg Ile Gly
1665                1670                1675                1680

Ser Ser Val Ile Ala His Glu Val Lys Leu Ser Ser Gly Glu Thr Arg
            1685                1690                1695

Trp Val Ile Asp Thr Ile Val Gly Lys Glu Asp Gly Ile Gly Val Glu
            1700                1705                1710

Asn Leu Thr Gly Ser Gly Ala Ile Ala Gly Ala Tyr Ser Lys Ala Tyr
            1715                1720                1725

Asn Glu Thr Phe Thr Leu Thr Phe Val Ser Gly Arg Thr Val Gly Ile
            1730                1735                1740

Gly Ala Tyr Leu Ala Arg Leu Gly Met Arg Cys Ile Gln Arg Leu Asp
1745                1750                1755                1760

Gln Pro Ile Ile Leu Thr Gly Phe Ser Thr Leu Asn Lys Leu Leu Gly
            1765                1770                1775

Arg Glu Val Tyr Ser Ser His Met Gln Leu Gly Gly Pro Lys Ile Met
            1780                1785                1790

Gly Thr Asn Gly Val Val His Leu Thr Val Ser Asp Asp Leu Glu Gly
            1795                1800                1805

Val Ser Ala Ile Leu Asn Trp Leu Ser Tyr Ile Pro Ala Tyr Val Gly
            1810                1815                1820

Gly Pro Leu Pro Val Leu Ala Pro Leu Asp Pro Pro Glu Arg Ile Val
1825                1830                1835                1840

Glu Tyr Val Pro Glu Asn Ser Cys Asp Pro Arg Ala Ala Ile Ala Gly
            1845                1850                1855

Val Lys Asp Asn Thr Gly Lys Trp Leu Gly Gly Ile Phe Asp Lys Asn
            1860                1865                1870

Ser Phe Ile Glu Thr Leu Glu Gly Trp Ala Arg Thr Val Val Thr Gly
            1875                1880                1885

Arg Ala Lys Leu Gly Gly Ile Pro Val Gly Val Val Ala Val Glu Thr
            1890                1895                1900

Gln Thr Val Met Gln Ile Ile Pro Ala Asp Pro Gly Gln Leu Asp Ser
1905                1910                1915                1920

His Glu Arg Val Val Pro Gln Ala Gly Gln Val Trp Phe Pro Asp Ser
            1925                1930                1935

Ala Ala Lys Thr Ala Gln Ala Leu Met Asp Phe Asn Arg Glu Glu Leu
            1940                1945                1950

Pro Leu Phe Ile Leu Ala Asn Trp Arg Gly Phe Ser Gly Gly Gln Arg
            1955                1960                1965
```

-continued

```
Asp Leu Phe Glu Gly Ile Leu Gln Ala Gly Ser Thr Ile Val Glu Asn
    1970                1975               1980

Leu Arg Thr Tyr Arg Gln Pro Val Phe Val Tyr Ile Pro Met Met Gly
1985                1990                1995                2000

Glu Leu Arg Gly Gly Ala Trp Val Val Val Asp Ser Gln Ile Asn Ser
                2005                2010                2015

Asp Tyr Val Glu Met Tyr Ala Asp Glu Thr Ala Arg Gly Asn Val Leu
            2020                2025                2030

Glu Pro Glu Gly Thr Ile Glu Ile Lys Phe Arg Thr Lys Glu Leu Leu
        2035                2040                2045

Glu Cys Met Gly Arg Leu Asp Gln Lys Leu Ile Ser Leu Lys Ala Lys
    2050                2055                2060

Leu Gln Asp Ala Lys Gln Ser Glu Ala Tyr Ala Asn Ile Glu Leu Leu
2065                2070                2075                2080

Gln Gln Gln Ile Lys Ala Arg Glu Lys Gln Leu Leu Pro Val Tyr Ile
                2085                2090                2095

Gln Ile Ala Thr Lys Phe Ala Glu Leu His Asp Thr Ser Met Arg Met
            2100                2105                2110

Ala Ala Lys Gly Val Ile Lys Ser Val Val Glu Trp Ser Gly Ser Arg
        2115                2120                2125

Ser Phe Phe Tyr Lys Lys Leu Asn Arg Arg Ile Ala Glu Ser Ser Leu
    2130                2135                2140

Val Lys Asn Val Arg Glu Ala Ser Gly Asp Asn Leu Ala Tyr Lys Ser
2145                2150                2155                2160

Ser Met Arg Leu Ile Gln Asp Trp Phe Cys Asn Ser Asp Ile Ala Lys
            2165                2170                2175

Gly Lys Glu Glu Ala Trp Thr Asp Asp Gln Val Phe Phe Thr Trp Lys
            2180                2185                2190

Asp Asn Val Ser Asn Tyr Glu Leu Lys Leu Ser Glu Leu Arg Ala Gln
            2195                2200                2205

Lys Leu Leu Asn Gln Leu Ala Glu Ile Gly Asn Ser Ser Asp Leu Gln
    2210                2215                2220

Ala Leu Pro Gln Gly Leu Ala Asn Leu Leu Asn Lys Val Glu Pro Ser
2225                2230                2235                2240

Lys Arg Glu Glu Leu Val Ala Ala Ile Arg Lys Val Leu Gly
                2245                2250
```